(12) United States Patent
Stavros et al.

(10) Patent No.: US 12,141,974 B2
(45) Date of Patent: *Nov. 12, 2024

(54) SYSTEM AND METHOD FOR DETERMINING A FEATURE GRADE FOR A PERITUMORAL FEATURE OF AN OPTOACOUSTIC IMAGE

(71) Applicant: Seno Medical Instruments, Inc., San Antonio, TX (US)

(72) Inventors: Anthony Thomas Stavros, San Antonio, TX (US); Reni S. Butler, New Haven, CT (US); Philip T. Lavin, Framingham, MA (US); Jason Zalev, Thornhill (CA); Thomas G. Miller, Houston, TX (US)

(73) Assignee: Seno Medical Instruments, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,648

(22) Filed: Apr. 4, 2023

(65) Prior Publication Data

US 2023/0245310 A1 Aug. 3, 2023

Related U.S. Application Data

(60) Continuation of application No. 17/166,313, filed on Feb. 3, 2021, now Pat. No. 11,651,489, which is a
(Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0035* (2013.01); *A61B 5/0095* (2013.01);
(Continued)

(58) Field of Classification Search
CPC .................................................. G06T 7/0012
See application file for complete search history.

(56) References Cited

U.S. PATENT DOCUMENTS 8,073,214 B2 * 12/2011 Hong .................... G06T 7/0012
  382/128
9,545,456 B2 * 1/2017 Oraevsky ............. A61B 5/0035
(Continued)

OTHER PUBLICATIONS

B. Menezes. "Downgrading of Breast Masses Suspicious for Cancer by Using Optoacoustics Breast Image" 2018; 288:355-365 https://doi.org/10.1148/radiol.2018170500, (Year: 2007).*
(Continued)

*Primary Examiner* — Oneal R Mistry
(74) *Attorney, Agent, or Firm* — Dean D. Small; The Small Patent Law Group, LLC

(57) ABSTRACT

The diagnostic vector classification support system and method disclosed herein may both reduce the time and effort required to train radiologists to interpret medical images, and provide a decision support system for trained radiologists who, regardless of training, have the potential to miss relevant findings. In an embodiment, a morphological image is used to identify a zone of interest in a co-registered functional image. An operator's grading of a feature at least partially contained within the zone of interest is compared to one or more computer-generated grades for the feature. Where the operator and computer-generated grades differ, diagnostic support can be provided such as displaying additional images, revising the zone of interest, annotating one or more displayed images, displaying a computer-generated feature grade, among other possibilities disclosed herein.

18 Claims, 16 Drawing Sheets

Related U.S. Application Data continuation of application No. 16/022,138, filed on Jun. 28, 2018, now Pat. No. 10,949,967, which is a continuation of application No. 15/213,889, filed on Jul. 19, 2016, now Pat. No. 10,026,170, which is a division of application No. 14/205,005, filed on Mar. 11, 2014, now Pat. No. 9,398,893.

(60) Provisional application No. 61/799,213, filed on Mar. 15, 2013, provisional application No. 61/810,238, filed on Apr. 9, 2013, provisional application No. 61/898,392, filed on Oct. 31, 2013.

(51) Int. Cl.
  *A61B 8/08* (2006.01)
  *G06F 18/2113* (2023.01)
  *G06F 18/241* (2023.01)

(52) U.S. Cl.
  CPC .......... *A61B 8/0825* (2013.01); *A61B 8/5223* (2013.01); *A61B 8/5261* (2013.01); *A61B 8/5292* (2013.01); *G06F 18/2113* (2023.01); *G06F 18/241* (2023.01); *A61B 2576/00* (2013.01); *G06T 2207/10132* (2013.01); *G06T 2207/30096* (2013.01)

(56) References Cited

U.S. PATENT DOCUMENTS

| | | | | |
|---|---|---|---|---|
| 2006/0120581 A1* | 6/2006 | Eck | ...................... | G06T 7/0016 382/128 |
| 2009/0082637 A1* | 3/2009 | Galperin | ................ | G16H 30/20 600/300 |
| 2009/0143676 A1* | 6/2009 | Matsumura | .......... | A61B 8/4444 600/443 |
| 2009/0306500 A1* | 12/2009 | Rahn | ...................... | G16H 30/40 600/431 |
| 2011/0245673 A1* | 10/2011 | Kamiyama | .......... | G01S 7/52071 600/443 |
| 2011/0270157 A1* | 11/2011 | Chance | ................. | A61M 37/00 604/66 |
| 2012/0300903 A1* | 11/2012 | Yao | ........................ | A61B 6/481 378/62 |
| 2013/0190595 A1* | 7/2013 | Oraevsky | .................. | A61B 8/483 600/407 |
| 2014/0003688 A1* | 1/2014 | Hansis | ................... | A61B 6/032 382/130 |
| 2014/0029817 A1* | 1/2014 | Gleichman | ........... | G06T 7/0012 382/131 |
| 2014/0073907 A1* | 3/2014 | Kumar | ............... | A61B 10/0241 600/407 |
| 2014/0093150 A1* | 4/2014 | Zalev | ..................... | A61B 5/726 382/128 |
| 2014/0301619 A1* | 10/2014 | Stavros | ................ | A61B 5/0035 382/131 |
| 2015/0148677 A1* | 5/2015 | Mullick | .................... | G06T 7/13 600/443 |
| 2015/0379709 A1* | 12/2015 | Liang | ....................... | G06T 7/60 382/131 |
| 2017/0091927 A1* | 3/2017 | Auvray | ................ | A61B 6/4441 |
| 2018/0053300 A1* | 2/2018 | Podilchuk | ............ | G06T 7/0016 |
| 2019/0275179 A1* | 9/2019 | Grimm | .................... | C07K 7/64 |

OTHER PUBLICATIONS

A. Khokhlova. "Optoacoustic imaging of absorbing objects in a turbid medium: ultimate sensitivity and application to breast cancer diagnostic" Applied Optics, vol. 46, No. 2 _ Jan. 10, 2007. (Year: 2018).*

* cited by examiner

| Examples of Feature Grades | Grade 0 | Grade 1 | Grade 2 | Grade 3 | Grade 4 | Grade 5 |
|---|---|---|---|---|---|---|

Image Data

| Lesion Classification | Feature 1 | Feature 2 | Feature 3 | Feature 4 | Feature 5 | Feature 6 |
|---|---|---|---|---|---|---|
| | | | Feature Grading | | | |

FIG. 6

| | | | | | | | | | | | | | |
|---|---|---|---|---|---|---|---|---|---|---|---|---|---|
| FEAS-PREF | F = FEASIBILITY | pF = PREFEASIBILITY | | | | | | | | | | | |
| EXCLUDE | Y = YES | N = NO | | | | | | | | | | | |
| EXCL REASON | MS = MISSING STUDY | WL = WRONG LESION | TI = TECHNICALLY INADEQUATE | EA = EXCESSIVE ARTIFACT | | | | | | | | | |
| HISTO GROUP | B = BENIGN | M = MALIGNANT | H = HIGH RISK | | | | | | | | | | |
| HISTO SPEC | IDC = INVASIVE DUCT CARCINOMA | ILC = INVASIVE LOBULAR CARCINOMA | CIS = CARCINOMA IN SITU | MC = MUCINOUS/COLLOID CAR | MCC = MUCINOUS/COLLOID CARCINOMA | LYM = LYMPHOMA | BBC = | | | | | | |
| | IPC = INVASIVE PAPILLARY CA | | LDP = LARGE DUCT PAPILLOMA | | | | | | | | | | |
| | FA = FIBROADENOMA | FCC = FIBROCYSTIC CHANGE | SCT = SCAR TISSUE | FN = FAT NECROSIS | HEM = HEMATOMA | IMN = INTRAMAMMARY LYMPH NODE | NORMAL | | | | | | |
| | ICC = INDETERMINATE CYST/SOLID | FI = INFLAMMATION | | | | | | | | | | | |
| | RS = RADIAL SCAR | ATH = A | | | | | | | | | | | |
| | PT = PHYLLODES TUMOR | | | | | | | | | | | | |
| HISTO GRADE | 1 = LOW GRADE | 2 = INTERMEDIATE GRADE | 3 = HIGH GRADE | | | | | | | | | | |
| CA SUBTYPE | ISN = MICROPAPILLARY C/S | ISO = SOLID C/S | ICR = CRIBIFORM C/S | | | | | | | | | | |
| B9 SUBTYPE | FAH = HYALINIZED FA | FAJ = FA CELLULAR STROMA (JUVENILE) | FAC = FA COMPLEX | | | | | | | | | | |
| | CYS = CYST | ACY = APOCRINE CYST | CLM = CLUSTERED MICROCYSTS | FSC = FIBROSCLEROSIS | UDH = DUCT HYPERPLASIA | AD = ADENOSIS | SCA = SCLEROSING ADENOSIS | | | | | | |
| INTERVAL W | 0 = NONE | 1 = UP TO ONE ARTERY AND ONE VEIN | 2 = UP TO ONE ART AND ONE V WITH MNR BRANCHES | 3) SPECKLE RED > GREEN = BKGD | 4) SPECKLE RED > GREEN > BACKGROUND | 5) MULTIPLE RED VESSELS | | | | | | | |

FROM FIG. 13A

FIG. 13B

SYSTEM AND METHOD FOR DETERMINING A FEATURE GRADE FOR A PERITUMORAL FEATURE OF AN OPTOACOUSTIC IMAGE

This application is a continuation of U.S. patent application Ser. No. 17/166,313, filed Feb. 3, 2021, which is a continuation of U.S. patent application Ser. No. 16/022,138, filed Jun. 28, 2018 (now U.S. Pat. No. 10,949,967, issued Mar. 16, 2021), which is a continuation of U.S. patent application Ser. No. 15/213,889, filed Jul. 19, 2016 (now U.S. Pat. No. 10,026,170, issued Jul. 17, 2018), which is a divisional of U.S. patent application Ser. No. 14/205,005, filed Mar. 11, 2014 (now U.S. Pat. No. 9,398,893, issued Jul. 26, 2016), which claims benefit of U.S. Provisional Patent Application No. 61/799,213 filed Mar. 15, 2013, U.S. Provisional Patent Application No. 61/810,238 filed Apr. 9, 2013, and U.S. Provisional Patent Application No. 61/898,392 filed Oct. 31, 2013. The entire disclosures of which are incorporated herein by reference in their entirety.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of medical imaging, and in particular to system relating to support for interpretation of optoacoustic imaging.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

The patent or application file contains at least one drawing executed in color. Copies of this patent or patent application publication with color drawing(s) will be provided by the U.S. Patent and Trademark Office upon request and payment of the necessary fee.

FIG. 6 is a diagram illustrating an embodiment of a graphical user interface for use in operator feature grading and lesion classification.

FIGS. 13A and 13B show the categories and rankings of various features in accordance with an embodiment of the subject invention.

Figure 1:
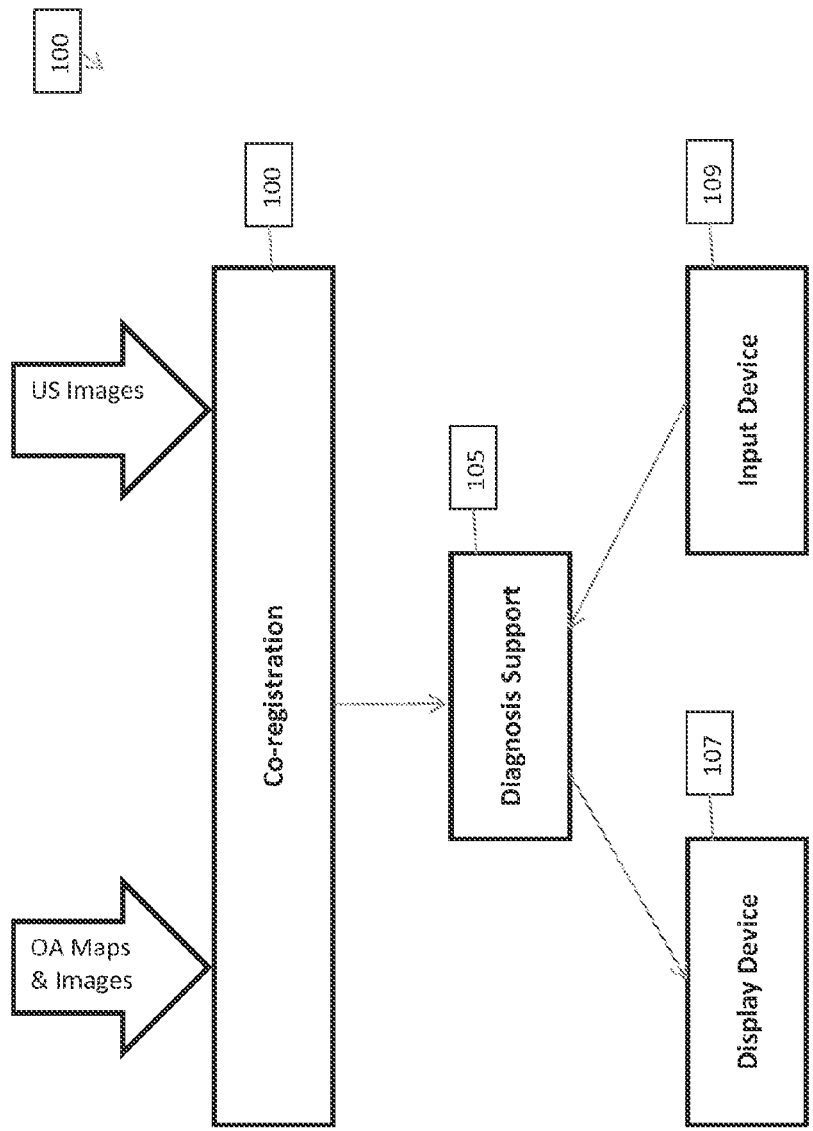
FIG. 1 is a schematic block diagram illustrating an embodiment of a system for use in support of diagnostic vector classification of lesions.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description and drawings are illustrative and are not to be construed as limiting. Numerous specific details are described to provide a thorough understanding. Yet, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

As used in this description and in the following claims, "a" or "an" means "at least one" or "one or more" unless otherwise indicated. In addition, the singular forms "a," "an," and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" (that is, both the conjunctive and the subjunctive) unless the context clearly dictates otherwise.

The recitation herein of numerical ranges by endpoints includes all numbers subsumed within that range (e.g. 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

The systems and methods are described below with reference to, among other things, block diagrams, operational illustrations and algorithms of methods and devices to process optoacoustic imaging data. It is understood that each block of the block diagrams, operational illustrations and algorithms and combinations of blocks in the block diagrams, operational illustrations and algorithms, can be implemented by means of analog or digital hardware and computer program instructions.

Computer program instructions described herein can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

In some alternate implementations, the functions/acts noted in the blocks can occur out of the order noted in the operational illustrations. For example, two blocks shown in succession can in fact be executed substantially concurrently or the blocks can sometimes be executed in the reverse or a differing order, depending upon the functionality/acts involved.

Diagnostic Vector Classification Support System

Radiology is a medical specialty that employs the use of imaging to diagnose and/or treat disease visualized within the human body. A radiologist interprets images created by any of a variety of medical imaging technologies, and produces a report of findings, impression and/or diagnosis. Radiologists are highly trained at interpreting one or more of the types of images created by various medical imaging technologies.

Optoacoustic imaging is a relatively new clinical field. Substantial time and effort is required to train a radiologist to interpret images created from optoacoustic data. The diagnostic vector classification support system and method disclosed herein may both reduce the time and effort required to train a radiologist to interpret images created from optoacoustic data, and provide a decision support system for trained radiologists who, regardless of training, have the potential to miss relevant findings. While the system described herein is shown with respect to images created from optoacoustic data, and specifically images created from ultrasound and optoacoustic data, it is not so limited, and is equally applicable to other types of medical images.

Turning first to FIG. 1, an embodiment of a diagnostic vector classification support system 100 is generally shown. In an embodiment, the system 100 is embodied as a processing subsystem of an imaging system, such as the multimodal optoacoustic and ultrasound system described in U.S. patent application Ser. No. 13/507,222, filed Jun. 13, 2013 and entitled "System and Method for Producing Parametric Maps of Optoacoustic Data" (hereinafter the "Parametric Map Application"). In an embodiment, the system 100 is implemented on a standalone system or general purpose computer, comprising the appropriate software and a user interface as described herein, adapted to process images produced by one or more separate imaging systems including separate or multimodal optoacoustic and or ultrasound systems. In this latter case, the images must be acquired from a suitable source of the images, or transferred to the system, e.g., via the Internet or by a storage medium and reader.

In an embodiment, a co-registration sub-system 103 obtains a plurality of images of a volume of tissue and spatially aligns the images. Such images may include images produced by various imagining technologies including but not limited to MRI, CT Scan, X-ray, Ultrasound, Optoacoustic, among other modalities. In an embodiment, as shown, structural images, such as those produced by ultrasound are spatially aligned with functional images, such as those produced by optoacoustic imaging. In embodiment, multiple optoacoustic images or parametric maps are spatially aligned. In an embodiment, the co-registration sub-system 103 is not required because the images obtained by the system 100 are already spatially aligned. In an embodiment, only portions of the images are spatially aligned. In an embodiment, the images are spatially aligned with known landmarks or annotations. For more detailed description of co-registration techniques, reference can be had to the Parametric Map Application.

In an embodiment, the spatially aligned images are received by a diagnosis support sub-system 105. In the embodiment as shown, the diagnosis support sub-system 105 is capable of presenting images and other output to an observer via a display device 107. In an embodiment, the display device 107 comprises a video monitor, screen, holographic display, printer, or other technology known in the art capable of presenting two and three dimensional images. In an embodiment, sound, haptic, or other output methods known in the art are used to convey information. In an embodiment, videos may be presented comprising both sound and images. In an embodiment, the diagnosis support sub-system 105 is capable of presenting information via multiple display devices.

In the embodiment as shown, the diagnosis support sub-system 105 is also capable to receiving classifications, scoring or other input from the observer or other operator via an input device 109. In an embodiment, the input device 105 comprises a pointing device such as a mouse, trackball, touch screen, or other pointing device. In an embodiment, the input device 105 comprises a keyboard, keypad, or other device for textual input. In an embodiment, the input device 105 comprises a microphone or other audio input device. Other input devices may be used. In an embodiment, the diagnosis support sub-system 105 is capable of receiving input from multiple input devices.

In an embodiment, the diagnosis support sub-system 105 identifies at least one feature of at least one image that is significant for diagnosis of a disease or condition. In an embodiment, the operator provides input to identify the feature. For example, the operator may select one or more pixels in at least one image corresponding to a structure or other significant region of the volume. As used throughout this specification and the below claims, the term "corresponding to" means an element of an image or parametric map spatially represents or provides information about a location or region in a volume of tissue, which term encompasses estimating and approximating of the location or region. Feature identification is further discussed below through the example of identification of a lesion or tumor in a volume of tissue.

In an embodiment, the diagnosis support sub-system 105 provides a qualitative or quantitative analysis of the at least one feature. In an embodiment, the operator or other user also provides a qualitative analysis of the at least one feature. In an embodiment, the results of the system's analysis are compared with the operator's conclusions. The operator may also provide additional input either before or after system's evaluation. For example, in an embodiment, the operator changes, augments or corrects the system's feature identification. In an embodiment, the operator confirms the system's evaluation. In an embodiment, the system displays additional images or other information to the operator before the additional input is received. For example, the system may display additional images of the volume (including images from other modalities), annotations highlighting or otherwise indicating image features, additional analysis of the feature, examples (e.g., images) of the feature as presented in other volumes of tissue, or evaluations of the feature obtained by different algorithms, models, or systems.

In an embodiment, the at least one feature comprises a lesion. In an embodiment, the at least one feature includes a feature vector including a plurality of features of the lesion. In embodiment, features found in an interior zone of an image corresponding to an interior region of the lesion are evaluated. In an embodiment, features found in an exterior or external zone of an image corresponding to a region of the volume exterior to the lesion are evaluated.

In an embodiment, images are segmented into three or more regions. In the example shown in FIG. 3, an optoacoustic image of a volume of tissue is divided into three regions using two boundary curves. The white, "tumoral" boundary curve defines an interior zone of the image corresponding to an interior region of the tumor. In an embodiment, the interior region of the tumor is defined by the central nidus of the tumor. In an embodiment, the central nidus is hypoechoic on ultrasound and the interior zone is identified on one or more ultrasound images of the volume, which can then be co-registered with optoacoustic images or other parametric maps of the volume.

Figure 3:
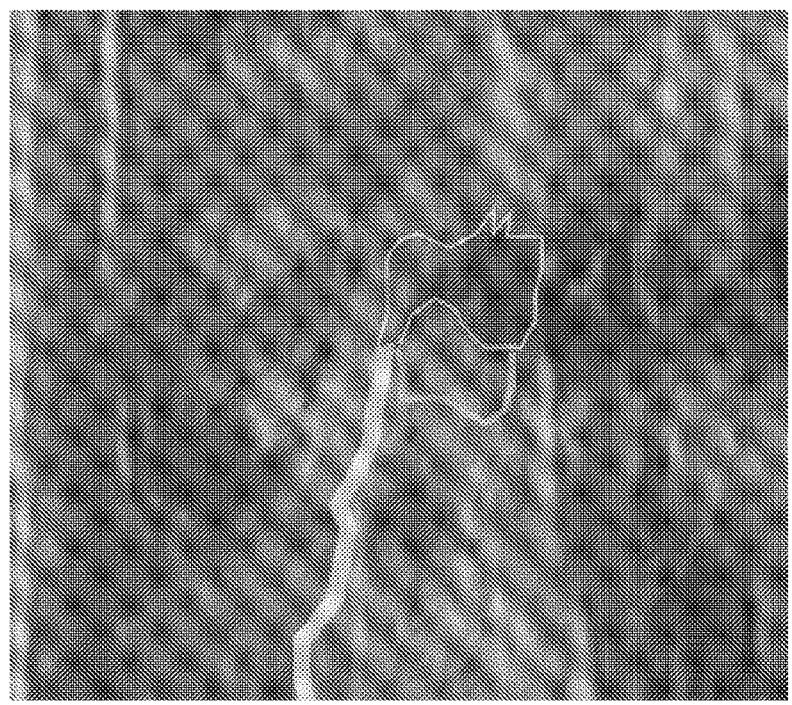
FIG. 3 shows an optoacoustic image with boundary curves displayed thereon in accordance with an embodiment of the invention.

FIG. 3 also includes a blue, "peritumoral" boundary curve corresponding to a periphery of a peritumoral region of the tumor adjacent to the central nidus. In an embodiment, a portion of an image between a tumoral and a peritumoral boundary curve is referred to as a "boundary zone" of the image. In an embodiment, more than one boundary zone may exist and correspond to regions of the volume outside but adjacent to the central nidus of a tumor. Boundary zones may not exist adjacent to each edge of the tumoral boundary curve. In an embodiment, the peritumoral boundary curve overlaps with the tumoral boundary curve where no separate boundary zone exists.

In an embodiment, the peritumoral and tumoral boundary curves are used to define at least three zones of an image corresponding to at least three regions of the volume: (1) an interior zone corresponding to the interior of the tumor; (2) a boundary zone corresponding to a peritumoral region of the volume adjacent to the tumor; and (3) an peripheral zone corresponding to a region of the volume outside both the tumoral and peritumoral regions of the tumor. A feature vector may include features from one or more of these zones. Such features may include, by way of example and not limitation: the internal vascularity of the lesion; internal deoxygenation of the lesion; the peritumoral boundary vascularity of the lesion; the peritumoral deoxygenation of the lesion; the internal de-oxygenated blush; the internal total blood; the external peritumoral radiating vessels; and the presence of one or more interfering artifacts among other possible features of the lesion. As further discussed below, in an embodiment, these and other features may appear and be evaluated on ultrasound images, optoacoustic images, parametric maps or other spatial representations of a volume of tissue.

In an embodiment, the diagnosis support sub-system 105 evaluates at least one feature of the lesion by analyzing one or more images or maps of the volume. In an embodiment, the diagnosis support sub-system 105 develops a qualitative or quantitative value based on its evaluation of the feature. In an embodiment, the evaluated features are part of a feature vector associated with the volume. In an embodiment, the evaluation of a feature comprises scoring the feature by trained or otherwise known feature grades.

In an embodiment, the diagnosis support sub-system 105 is adapted to permit identification of a lesion within the volume, to obtain operator and computer classification of the lesion, to compare the classifications, and to provide diagnostic support where the computer and operator classifications differ. In an embodiment, diagnostic support is provided even where the computer and operator reach the same classifications.

In an embodiment, the computer classification of the lesion is based on evaluation of a vector of features of the volume associated with the lesion. In an embodiment, the diagnosis support sub-system 105 guides the user through a process for evaluating multiple features of the volume within the feature vector. In an embodiment, the diagnosis support sub-system 105 presents information about each of the features in parallel (e.g., using different portions of the display device 107). An example user interface is provided in FIG. 6. In an embodiment, the diagnosis support sub-system 105 presents information about each of the features in series. For example, in embodiment, the diagnosis support sub-system 105 causes the display device 107 to highlight or otherwise annotate portions of images of the volume that the diagnosis support sub-system 105 used to evaluate each feature in the volume. The diagnosis support sub-system 105 may then solicit the user's evaluation of the feature or other input.

The user may use the sub-system 105's annotating to reach the user's own conclusions about each feature. In an embodiment, the sub-system 105 displays such annotations in response to the user's evaluation when the user's evaluation differs or differs substantially from the sub-system 105's evaluation of a feature. In an embodiment, the user input may comprise a correction of the zone of an image that the diagnosis support sub-system 105 used to evaluate one or more features in the feature vector. In an embodiment, for example, the user may correct or augment one of the boundary curves used to define the periphery of the lesion and the diagnosis support sub-system 105 re-evaluates on or more features of the lesion based on the corrected periphery.

In an embodiment, the diagnosis support sub-system 105 displays or otherwise presents its own evaluation of one or more features to a user via the display device 107. In an embodiment, the diagnosis support sub-system 105 displays or highlights the features of the images or maps analyzed to produce an evaluation. In an embodiment, the diagnosis support sub-system 105 presents this information to the user in response to input from the user. In an embodiment, the user inputs the user's own evaluations of the feature, via the input device 109, before or after the diagnosis support sub-system 105 presents its evaluations. In an embodiment, the sub-system 105 displays its evaluations when the user's evaluation differs or differs substantially from the sub-system 105's evaluation.

In an embodiment, the diagnosis support sub-system 105 may also display other information that may be helpful to the user in evaluating the feature. For example, the sub-system 105 may display images a subject matter expert or other actor previously used to evaluate the same feature (in this or other volumes of tissue). In an embodiment, the sub-system 105 may display images that produced an evaluation similar to the sub-system 105's evaluation of the feature. In the embodiment, the sub-system 105 may display images that produced an evaluation similar to the user's evaluation of the feature. In an embodiment, the sub-system 105 then solicits input from the user regarding the feature. For example, in an embodiment, the sub-system 105 asks the user to confirm or change the sub-system 105's evaluation of the feature.

In an embodiment, the diagnosis support sub-system 105 computes a feature vector for a lesion based on the sub-system 105's and/or the user's evaluations of features in the vector. In embodiment, the results of the sub-system 105's computation are presented to the user. In an embodiment, the results include a suggested classification of the lesion. In an embodiment, the user inputs the user's own classification of the lesion before or after the sub-system 105 presents its classification. In an embodiment, the user is given the opportunity to confirm or modify the sub-system 105's classification of the lesion. If the user's classification of the lesion differs or differs substantially from the sub-system 105's classification, the sub-system 105 may present additional information and/or solicit additional user input. In an embodiment, the sub-system 105 only presents such additional information or solicits such additional user input of the difference between the operator's and the subsystem's feature grades would change the sub-system's classification of the feature.

Obtaining Images

Figure 2:
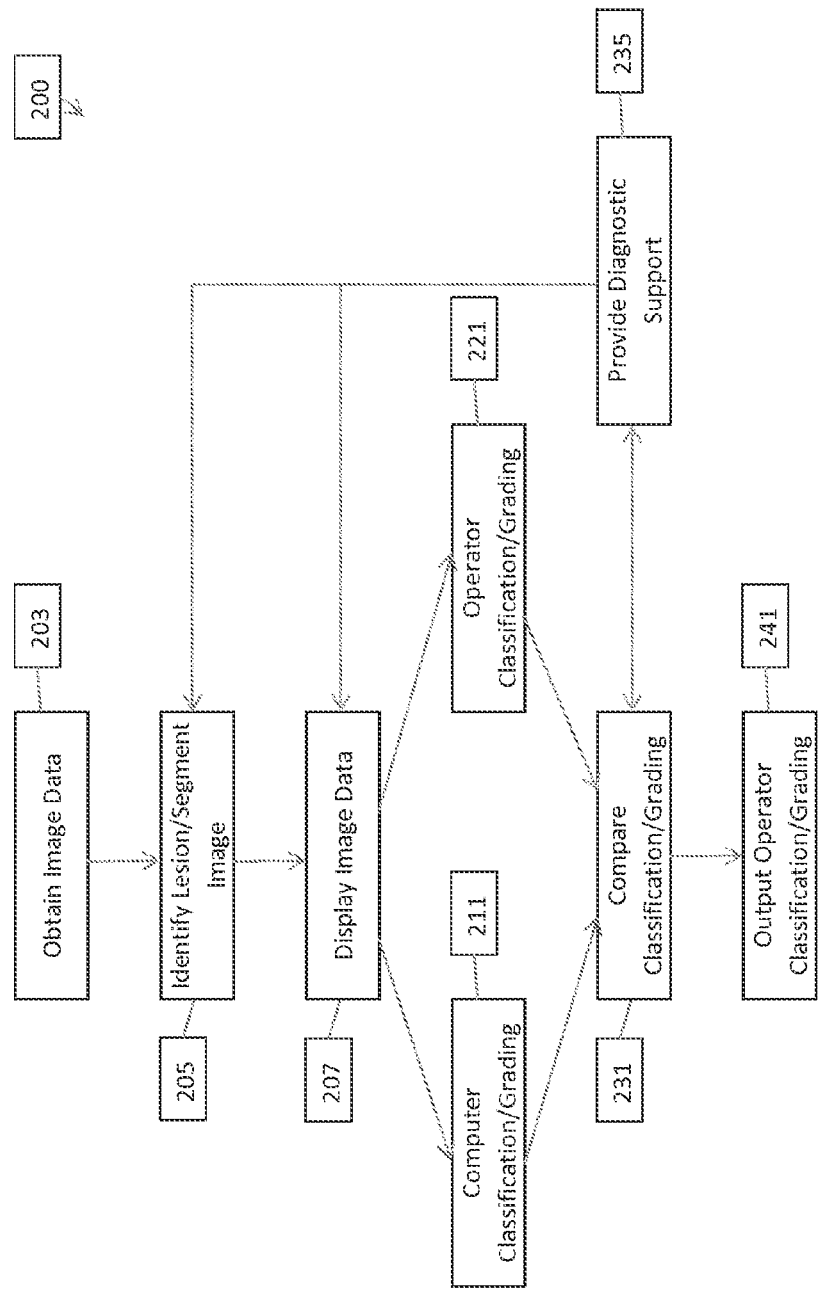
FIG. 2 is a flow diagram illustrating an embodiment of a process for diagnostic vector classification support.

Turning to FIG. 2, an embodiment of a diagnostic vector classification support method 200 is generally shown. At 203, an image is obtained from a source of such images, such as a multimodal optoacoustic and ultrasound system such as one described in the Parametric Map Application. In an embodiment, the image data may comprise one image. In an embodiment, the image data may comprise a plurality of images. Most of the examples shown herein are two-dimensional images or maps; however, the systems and methods discussed herein may also be applied to three or more dimensional representations of a volume of tissue.

In an embodiment where the image data is made up of a plurality of images, it is convenient to have the plurality of images co-registered. In an embodiment, the image data comprises radiological information of a volume of tissue. In an embodiment, the images of the image data depict visible functional or morphological structures in the volume (as they are available to be depicted by the modality of each image). In an embodiment, the image data comprises six images as generally reflected in FIG. 4.

Figure 4:
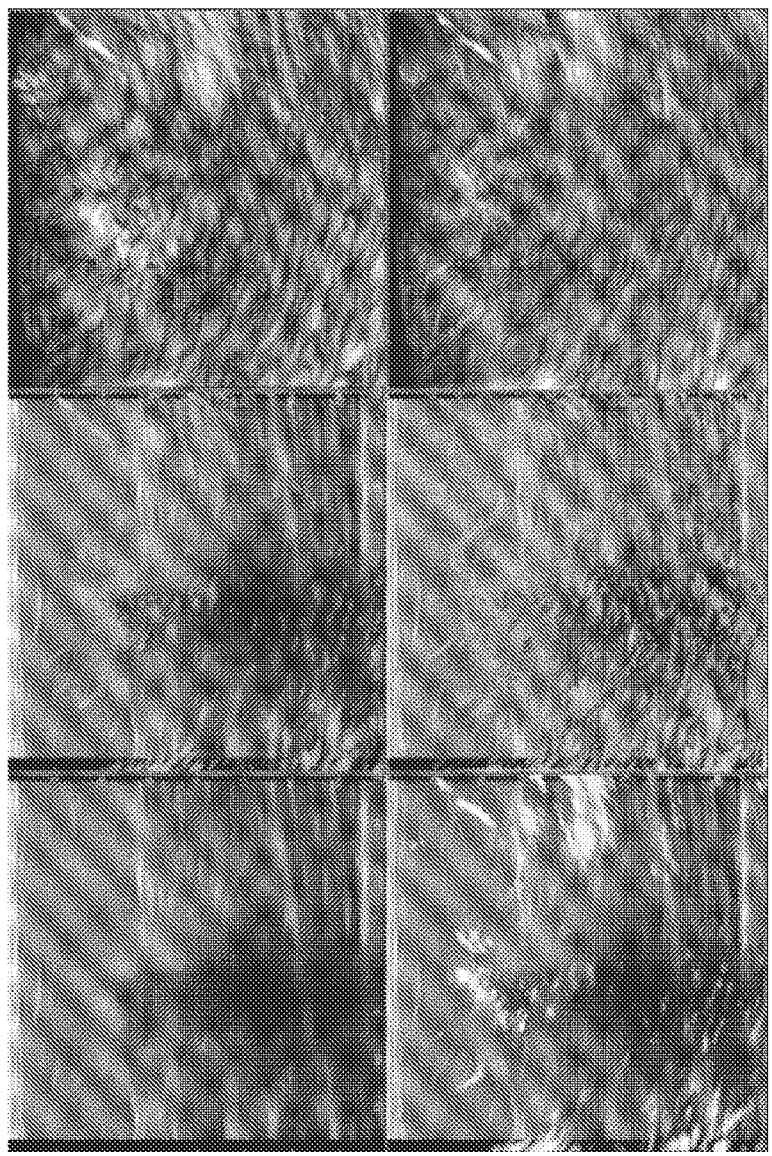
FIG. 4 is a six image display illustrating an embodiment of image data for use in support of diagnostic vector classification of lesions.

FIG. 4 illustrates six co-registered two-dimensional images: one comprising image information derived from ultrasound 410 ("ultrasound"); one comprising image information derived from optoacoustic imaging, and representative of the response of a longer predominant wavelength of light 420 ("long wavelength image"); one comprising image information derived from optoacoustic imaging, and representative of the response of a shorter predominant wavelength of light 430 ("short wavelength image"); and three being multimodal images comprising image information derived from optoacoustic imaging, one being parametrically reflective of total hemoglobin 440 ("total hemoglobin map"), one being parametrically reflective of deoxygenated hemoglobin 450 ("relative optoacoustic map"); and one being parametrically reflective of deoxygenated hemoglobin 450 masked using the image 440 parametrically reflective of total hemoglobin 460 ("combined optoacoustic map"). For more detailed description of the six image types, references can be had to the Parametric Map Application.

Identification of a Lesion/Image Segmentation

In an embodiment, at 205, a lesion or tumor is identified in the image data obtained at 203. The process of identifying a lesion in an image may vary depending on the type of image obtained for classification. In an embodiment, generally speaking, the goal is to define a perimeter, and potentially a periphery of a lesion as accurately as possible. Proper identification of a lesion perimeter aids in determination of whether a finding is internal or external to the lesion. In an embodiment, morphological images, such as ultrasound, are used to identify features corresponding to structures in a volume of tissue. Such features can then be used to segment the morphological image. In an embodiment, such segmentation is then applied to co-registered spatial representations of the same volume.

In an embodiment, the image(s) are segmented into two or more regions or zones. In an embodiment, segmentation involves outlining or otherwise identifying the boundaries of the lesion. In an embodiment, a lesion in an ultrasound image (e.g., conventional ultrasound image 410) may be segmented. In an embodiment, a lesion in an optoacoustic image may be segmented (e.g., images 420, 430, 440, 450, 460). Generally, an image needs to contain sufficient information to be capable of being segmented.

In an embodiment, segmentation is done by a trained operator, such as, for example, a radiologist. In an embodiment, the image or parts of the image are displayed on a computer screen and a trained operator carefully segments the boundary of the lesion on the display (e.g., by drawing or manipulating a mouse or other pointing device to select at least one point on or near the boundary), relying on the data present in the image. In an embodiment, multiple, co-registered images may be used as the source of information for segmentation and the trained operator can rely upon the data from, e.g., multiple images and/or modalities, to determine segmentation. In an embodiment, a first boundary is identified. In an embodiment, the first boundary is a tumoral boundary as described with reference to FIG. 3.

Figure 5:
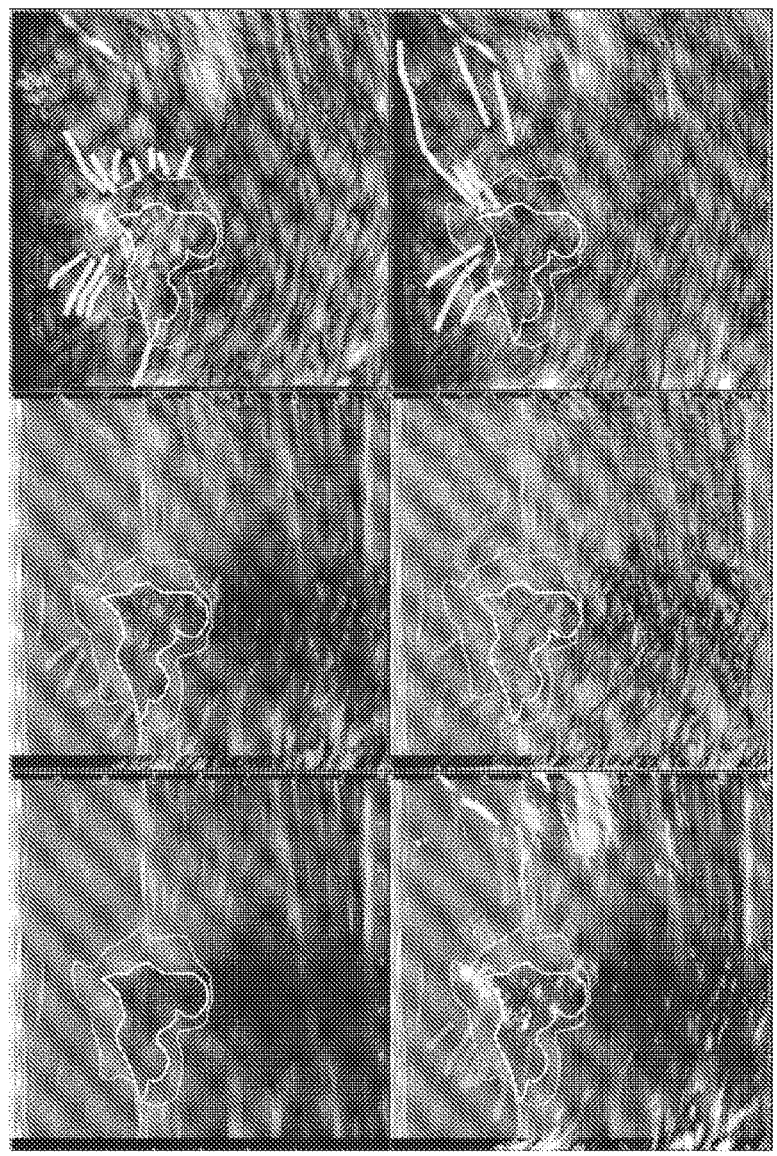
FIG. 5 is a six image display with boundary curves presented thereon in accordance with an embodiment of the invention.

FIG. 5 illustrates the same images shown in FIG. 4, however the images in FIG. 5 each include a white curve representing a tumoral boundary. The boundaries can also be represented by points, dashed lines, or other annotations. Note that while an operator may have identified the tumoral boundary, e.g., on the ultrasound image 410, a diagnostic vector classification support system can display the tumoral boundary on other images (e.g., images 420, 430, 440, 450, 460) as shown here. In an embodiment, an operator may provide a rough approximation of the lesion (e.g., a square, rectangle, circle, triangle, incomplete set of points, or freehand sketch) rather than carefully identifying its boundaries. Where the operator provides such a rough segmentation, as described in more detail below, the boundaries of the lesion can be more precisely estimated through the use of a segmentation technique implemented in the diagnostic vector classification support system. In an embodiment, if the diagnostic vector classification support system refines, adjusts or otherwise changes the approximation of the user, the user can further refine, adjust or otherwise change the diagnostic vector classification support system's results, leaving the ultimate selection of the boundary to the operator.

In an embodiment, a second boundary is identified outside the first boundary. In the embodiment shown in FIG. 5, a blue curve also appears in each image approximating a peritumoral boundary in the depicted image. The techniques discussed above with respect to identification of the first boundary may also be applied to identification of the second boundary. As above, although the second boundary curve may have been identified only on one of the images (e.g., ultrasound), the diagnostic vector classification support system can display the second boundary on multiple images. In an embodiment, the second boundary curve is used to define a peripheral region of the lesion between itself and the first boundary curve. As with the first boundary, in an embodiment, the second boundary can be drawn or otherwise identified by an operator, or may be generally (e.g., roughly) identified and made more precise by the use of a computer implemented segmentation technique. In an embodiment, the second boundary is identified automatically by a computerized process. In an embodiment, the second boundary is defined in relation to the first boundary. In an embodiment, the second boundary is a fixed distance away in the outward normal direction of the first boundary. The outward normal direction of the first boundary at a given point on the boundary is perpendicular to the tangent vector of the first boundary at the given point, such that in most circumstances the outward normal direction will point away from the interior region of the region enclosed by the first boundary.

In an embodiment, as with the first boundary, if the diagnostic vector classification support system itself identifies the second boundary, or if it refines, adjusts or otherwise changes the user's identification of the second boundary, the user can further refine, adjust or otherwise change the diagnostic vector classification support system's results, leaving the ultimate identification of the second boundary to the operator.

In an embodiment, the region inside the tumoral boundary is referred to as the interior region (i.e. internal zone), and the region outside the tumoral boundary but inside the peritumoral boundary is the peritumoral or boundary zone. The region outside the peritumoral boundary is referred to as the peripheral region.

Returning to FIG. 3, the image has been segmented into three zones. The white "tumoral" curve segments the image into an internal zone corresponding to the interior or central nidus of the represented tumor and an external zone corresponding to regions of the represented volume external to the central nidus of the represented tumor. The blue "peritumoral" curve further segments the external (or exterior) zone into a boundary (or peritumoral) zone and a peripheral zone. In an embodiment, the boundary zone corresponds to a portion of the represented volume adjacent to but outside the central nidus of the tumor. In an embodiment, the boundary zone varies in thickness and can be absent along some surfaces of the tumor. In an embodiment, the peritumoral boundary curve corresponds to a thick hyperechoic halo that can be identified on ultrasound images of the volume. In an embodiment, the peripheral zone corresponds to portions of the volume external to both the central nidus of the tumor and the boundary zone. In an embodiment, the peripheral zone is further from the central nidus than the boundary zone in an outward normal direction with respect to the tumor. In the image shown in FIG. 3, a think yellow line annotates a feature within the peripheral zone.

In an embodiment, features are evaluated which fall within various zones of the obtained images corresponding to various regions of the represented volume. In an embodiment, a feature is considered to fall within a particular zone if the feature is partially contained within that zone. So, for example, in an embodiment, a boundary zone feature may extend from the boundary zone into the peripheral zone. Or a structure considered to be in the peripheral region of a volume of tissue may extend into a peritumoral region of the volume.

In an embodiment, the boundary zone is considered an important source of information pertaining to classification of a tumor for at least three reasons: (1) it is where the tumor grows and invades surrounding tissue; (2) it is where the host response tries to stop the tumor from spreading; and (3) it is where cancer cells can convert some host cells (fibroblasts and macrophages) into cancer cells thereby helping the cancer grow. Further, the boundary zone may feature radiating feeding arteries and draining veins that supply the tumor with blood and oxygen and remove wastes from the tumor. Sometimes these vessels are parasitized native vessels and sometimes they are tumor neovessels.

In an embodiment, the boundary zone is very complex and may have many contributors to its appearance including: proliferating and invading tumor cells; a rich network of tumor neovessels, most of which are oriented near a 90 degree angle relative to the surface of the tumor (these neovessels are sometimes referred to a boundary zone "whiskers"); tumor associated collage type 3 fibers, which are also oriented perpendicular to the surface of the tumor; tumor associated macrophages; native lymphocytes sent to control the tumor; desmoplasia—fibrous tissue built by the host to create a wall around the tumor; edema—caused by fluid from abnormal tumor vessels; or proteinaceous debris from abnormal tumor vessels. A thin boundary or capsule zone may correspond to a benign lesion, while a thick boundary zone indicated by a thick echogenic halo may correspond to an invasive lesion.

In most cases of invasive cancer, a trained technician can identify the boundary zone on ultrasound images because it differs in echogenicity from both the central hypoechoic nidus and from the surrounding normal tissue. Echogenicity can be thought of as a mechanical property of the tissue. Features of co-registered optoacoustic images may also help identify the boundary zone in some cases. For example, some optoacoustic images show differences in the boundary zone (or capsule zone) of malignant lesions when compared to benign regions: Malignant lesions tend to have short perpendicular oriented tumor neovessels termed "boundary zone whiskers," while benign lesions tend to exhibit either the complete absence of boundary zone or capsular vessels or have long curved vessels oriented parallel to the surface of the tumor or capsule, rather than the more perpendicular orientation of most malignant vessels. Capsular vessels tend to be close in or touching the outer edge of the central nidus. Boundary zone vessels tend to be shorter and more perpendicular in orientation. In some cases, capusular vessels may be within about 1 to 3 mm of the central nidus. In other cases, capsular vessels may appear further away from the central nidus. Peripheral vessels may also appear farther out than the boundary zone. Peripheral vessels generally do not touch the central nidus and may or may not touch the boundary zone. Peripheral vessels generally radiate from the central nidus in a direction roughly perpendicular to the surface of the central nidus. Examples of possible boundary zone whiskers are annotated with orange lines in FIG. 5. Examples of possible radiating vessels are annotated with yellow lines in FIG. 5.

In an embodiment, as shown in FIG. 5, two closed boundary curves are calculated or otherwise obtained that completely define a zone of an image. In this case, the boundary zone can be defined by subtracting the zone defined by the inner boundary from the zone defined by the outer boundary. In an embodiment, first and second boundaries obtained may only define a portion of the lesion's interior and periphery. For example, in an embodiment, first and second boundaries only define the upper portion of a lesion—that is, the portion of the lesion closer to the sensor. Such an embodiment may be necessitated where the entire lesion does not appear in each of the images or where insufficient detail to identify the boundaries is found due to a decrease of information available below a certain depth of the lesion.

In an embodiment, one open and one closed boundary curve may be obtained. In an embodiment, the open boundary curve can be closed by connecting its end-points. In an embodiment, where the closed curve represents the tumoral boundary, as shown in FIG. 3, various methods can be used to connect the open boundary curve to the tumoral boundary. For example, in an embodiment, image context is used to draw connecting curves from the open boundary curve to the tumoral boundary. In an embodiment, connecting lines are drawn from each end-point of the boundary curve to the closest point on the tumoral boundary curve. In an embodiment, connecting lines are drawn from each end-point of the boundary curve that intersect the tumoral boundary curve at a perpendicular angle. Where multiple points on the tumoral boundary curve meet these criteria, the connecting point may be selected in various ways including the point closest or furthest from the end-point, the point closest or furthest from the center of the tumor, the point that creates the connecting line most perpendicular to the surface of the tumor.

In another embodiment, two open boundary curves may be obtained. In an embodiment, where two open boundary curves are obtained, the tumoral boundary curve can be closed by connecting its end-points or another technique known in the art, and then one or more of the techniques discussed above can be applied. In an embodiment, for each end-point of the peritumoral boundary curve, a line is drawn to the closest end-point of the tumoral boundary curve. In an embodiment, image context can be used to select the connecting points. Other techniques known in the art that can be applied. In an embodiment, first connecting lines are drawn using one or more of the techniques discussed above; and image context is then used to correct the straight connecting lines, which may therefore become connecting curves.

Displaying Image Data

In an embodiment, at 207, image data is displayed to an operator for analysis and input. In an embodiment, as discussed above, image data may be displayed for the purpose of segmentation. In an embodiment, image data is displayed or re-displayed after segmentation along with curves, dotted lines, highlights, or other annotations indicating one or more boundaries used to segment the images. In an embodiment, an operator may adjust one or more boundary curves at this time via the input device 109.

In an embodiment, image data is displayed by means of a display device such as display device 107. In an embodiment, image data may comprise multiple co-registered images of the volume as discussed above. In an embodiment, examples of feature representations from the same or other volume of tissue are displayed for comparison. In an embodiment, features from prior imaging of the same patient are displayed for progress or trend analysis. For example, prior imaging of the same patient can be displayed to track the progression of a disease such as cancer including tumor classification, growth, vascularity, total blood, and other features. In an embodiment, canonical examples of features exhibiting various grades or scores are shown. In an embodiment, image data is displayed via a graphical user interface such as that shown in FIG. 6. In an embodiment, as further discussed below, image data is displayed for evaluation, re-evaluation and operator input regarding tumor classification and/or image features.

Lesion Classification

In an embodiment, once image segmentation (205) is complete, classification may occur either by computer-generated classification (211), operator classification (221), or both. In an embodiment, image data need not be displayed to an operator (207) before computer classification/grading may occur (211).

In an embodiment, internal, periphery and external findings may be used to classify a lesion. In an embodiment, the interior region and the peripheral region of a lesion may be used to classify the lesion. In an embodiment, a plurality of features may graded using a scale, such as an ordinal scale. In an embodiment, a vector formed from the separately graded features corresponds to a likely classification or diagnosis. In an embodiment, multiple possible feature vectors can suggest a single classification.

In an embodiment, classification is done by assessing six specific features of optoacoustic images or other parametric maps on an ordinal scale, namely:
  1) internal vascularity and de-oxygenation,
  2) peritumoral boundary zone vascularity and deoxygenation,
  3) internal deoxygenated blush,
  4) internal total blood,
  5) external peritumoral radiating vessels, and
  6) interfering artifact.

In an embodiment, the six specific features are graded on an ordinal scale from 0-5. In an embodiment, the one or more features are graded on an ordinal scale from 0-6. Particular vectors of these feature scores have been shown to correlate with particular lesion classifications. In an embodiment, feature grades are summed to obtain a total internal score, a total external score, and/or a total overall score. In embodiment, a two-sided exact Jonckheere-Terpstra test is used to test the relationship between increasing scores (internal, external, total) and higher cancer grade.

In an embodiment, other features can be graded in addition to, or in lieu of one or more of the six specific features identified above including, but not limited to, internal, peritumoral, and peripheral:
  a) vascularity;
  b) density of vascularity;
  c) oxygenation;
  d) speckle;
  e) blush;
  f) amount of hemoglobin;
  g) amount of blood;
  h) ratio of oxygenated to deoxygenated blood;
  i) blood oxygen saturation;
  j) total blood accumulation; and
  k) amount of interfering artifacts.

Additional features can be evaluated in both the peritumoral and peripheral region including, but are not limited to:
  l) amount of tumor neovessels;
  m) amount of vessels oriented substantially parallel to a surface of the tumor;
  n) amount of vessels oriented substantially perpendicular to a surface of the tumor;
  o) length of vessels; and
  p) straightness of vessels.

Additional peritumoral features can be evaluated including, but not limited to:
  q) amount of proliferating tumor cells;
  r) amount of invading tumor cells;
  s) amount of tumor associated macrophages;
  t) amount of native cells that have been affected by the tumor;
  u) amount of lymphocytes;
  v) amount of desmoplasia;
  w) amount of edema;
  x) amount of proteinaceous debris;
  y) thickness of boundary zone; and
  z) amount of tumor associated collage type 3 fibers oriented substantially perpendicular to a surface of the tumor.

Additional peripheral features can be evaluated including, but not limited to:
  aa) amount of radiating arteries; and
  bb) amount of radiating veins.

In an embodiment, molecular indicators are graded in addition to grading some or all of the features identified above.

Operator Feature Grading

In an embodiment, at 221, an operator, generally a radiologist is presented with image data related to a lesion, and is prompted to enter a score for one of more features related to the lesion. In an embodiment, the image data presented to the user comprises one image. In an embodiment, the image data may comprise a plurality of images. In an embodiment where the image data is made up of a plurality of images, it is convenient to have the plurality of images co-registered. In an embodiment, the image data comprises radiological information of a volume of tissue. In an embodiment, the images of the image data depict visible functional or morphological structures in the volume (as they are available to be depicted by the modality of each image). In an embodiment, the image data comprises six images as generally reflected in FIG. 4. In an embodiment, the image data comprises boundary curves and/or other annotations superimposed one or more images of the volume as depicted in FIGS. 3 and 5.

In an embodiment, the operator is presented with a graphical user interface ("GUI") such as the interface reflected in FIG. 6. In an embodiment, the GUI includes an interface for feature grading. In the embodiment shown in FIG. 6, the interface for feature grading appears along the bottom portion of the GUI and allows the user to input grades for each of six features related to the lesion (grades for additional or fewer features can be solicited). In an embodiment, the operator may provide input on the grading of one or more features of the lesion via the interface. In an embodiment, the operator selects or inputs an ordinal grade for one or more features on a scale of 0-5 (other scales may be used). In an embodiment, the system presents the operator with one or more suggested feature grades based on analysis previously performed by the system and/or another user. In an embodiment, the operator can confirm or modify the suggested feature grades. In an embodiment, to change the focus of user input, the operator may click on an area of the screen devoted to receiving input for a particular feature or the operator may tab between feature inputs.

In an embodiment, in addition to the image data, the operator is also presented with example images depicting one or more grades for a particular feature. In the embodiment shown in FIG. 6, the example images appear along the right portion of the GUI and depict ordinal grades from 0 to 5. In an embodiment, the example images show lesions exhibiting possible grades for the feature. The examples may include image data previously collected from the current patient or other subjects. In an embodiment, the examples include images a subject matter expert or other user previously used to evaluate the same feature (in this or other volumes of tissue). In an embodiment, the system displays images that produced a score matching or similar to the system's calculated grading of the feature. In the embodiment, the system displays images that produced a score matching or similar to the operator's inputted grade of the feature. In embodiment, the examples include illustrations showing idealized presentations of the feature grades. In an embodiment, the examples depict only a portion of the lesion such as the portion relevant to the feature being graded. For instance, for internal deoxygenated blush the examples may just depict the area internal to the example lesions. Or the examples may just depict the portion of the internal area exhibiting blush. In an embodiment, the examples shown depend on the particular feature for which the system is currently seeking a grade (i.e., the feature currently in focus). In an embodiment, the operator may indicate the grading of the feature currently in focus by clicking on or otherwise selecting one of the depicted examples. In an embodiment, the examples shown change as the operator tabs or otherwise selects a different feature for grading. In an embodiment, the same example images are used but annotations (such as highlighting) are added to emphasize information relevant to the feature currently in focus.

In an embodiment, an operator applies guidelines for interpretation of image data. In an embodiment, such guidelines may be based on example or reference images as further exemplified below with reference to FIGS. 7-12. The reference images and guidelines discussed here are illustrative examples. Other types of images, guidelines, and features may be used.

Figure 7:
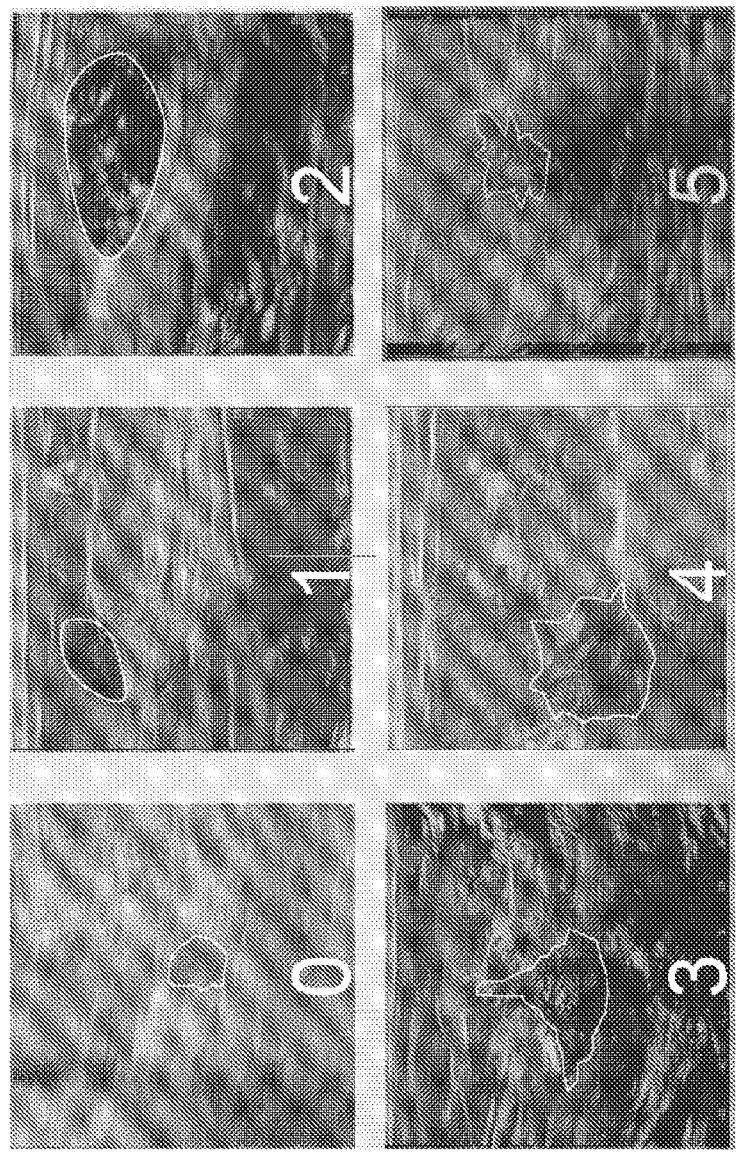
FIG. 7 shows six optoacoustic, combined map images illustrating examples of a feature internal vascularity in accordance with an embodiment of the subject invention.

FIG. 7 shows reference images for internal vascularity grades 0-5 on combined optoacoustic maps. In an illustrative embodiment, grade 0 is characterized by no internal vessels; grade 1 is characterized by up two internal vessels with no more than one red vessel (indicating a vessel carrying deoxygenated hemoglobin); grade 2 is characterized by up two internal vessels with branches and all or most branches being green (indicating a vessel carrying oxygenated hemoglobin); grade 3 is characterized by internal speckle with the amount of internal green and red speckle being substantially equal and less than the amount of exterior speckle; grade 4 is characterized by moderate internal speckle with the amount of internal red speckle being greater than the amount of internal green speckle and the amount of internal red speckle being greater than the amount of exterior red speckle; grade 5 is characterized by multiple internal red vessels.

Figure 8:
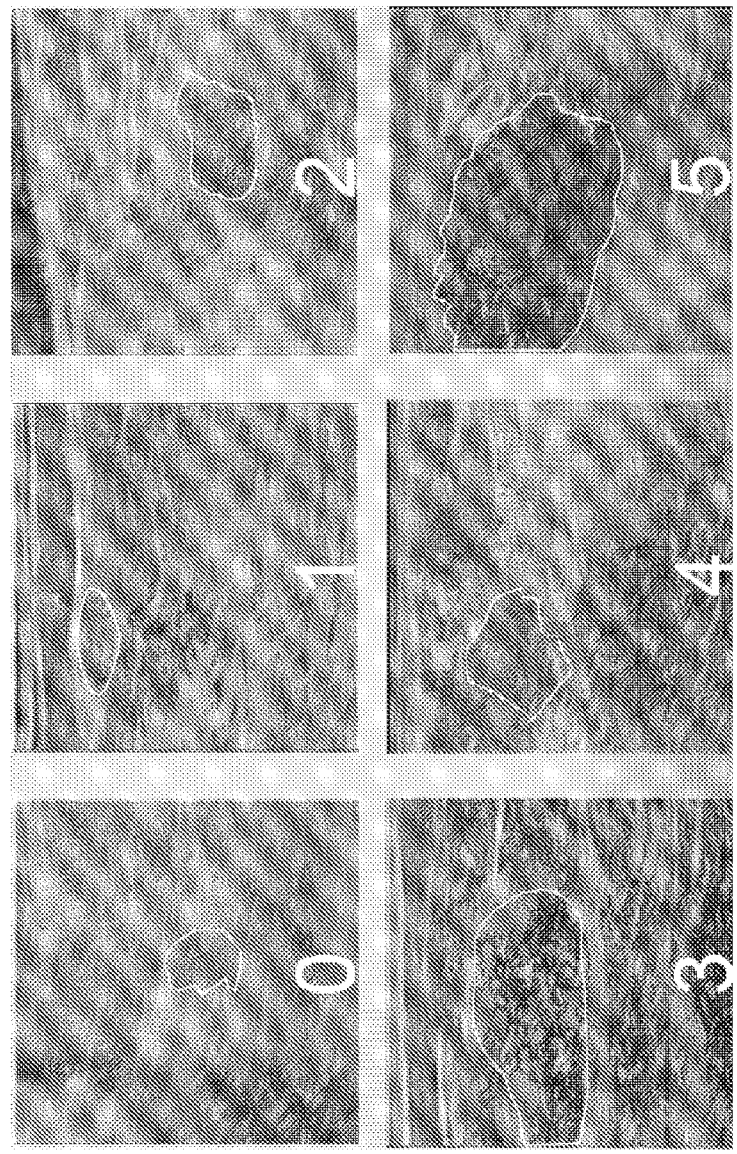
FIG. 8 shows six optoacoustic, combined map images illustrating examples of a feature internal blush in accordance with an embodiment of the subject invention.

FIG. 8 shows reference images for internal blush grades 0-5 on relative optoacoustic maps. In an illustrative embodiment, grade 0 is characterized by no internal vessels; grade 1 is characterized by minimal internal speckle all of which is green; grade 2 is characterized by mild internal speckle with green and red speckle being substantially equal and both red and green internal speckle together being less than or equal to the amount of exterior speckle; grade 3 is characterized by mild internal speckle with the amount of internal red speckle being greater than the amount of internal green speckle and both red and green internal speckle together being less than or equal to the amount of exterior speckle; grade 4 is characterized by moderate internal speckle with the amount of internal red speckle being greater than the amount of internal green speckle and the amount of internal red speckle being greater than the amount of exterior red speckle; grade 5 is characterized by internal red blush almost filling the internal zone.

Figure 9:
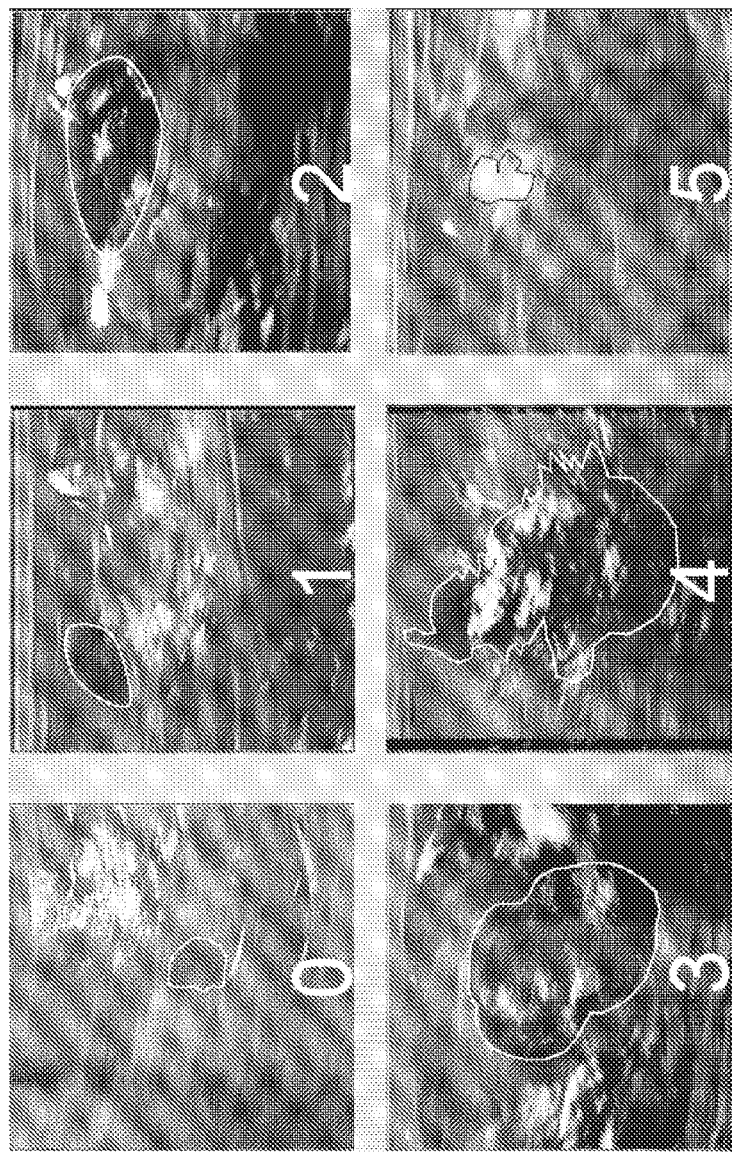
FIG. 9 shows six optoacoustic, hemoglobin map images illustrating examples of a feature internal hemoglobin in accordance with an embodiment of the subject invention.

FIG. 9 shows reference images for internal hemoglobin grades 0-5 on total hemoglobin maps. In an illustrative embodiment, grade 0 is characterized by no internal vessels; grade 1 is characterized by minimal internal hemoglobin which is less than or equal to external hemoglobin; grade 2 is characterized by a minimal number of internal discrete vessels with internal vascularity substantially equal to exterior vascularity; grade 3 is characterized by a moderate number of internal discrete vessels with internal vascularity substantially equal to exterior vascularity; grade 4 is characterized by many large internal vessels with internal vascularity greater than exterior vascularity; grade 5 is characterized by many large and heterogeneous vessels almost filling the internal zone.

Figure 10:
FIG. 10 shows seven optoacoustic images illustrating examples of a feature presence of capsular or boundary zone vessels in accordance with an embodiment of the subject invention.

FIG. 10 shows reference images for capsular/boundary zone vessel grades 0-6 shown on a various optoacoustic maps. In an illustrative embodiment, grade 0 is characterized by no capsular vessels (vessels oriented parallel to the surface of the tumor); grade 1 is characterized by up to two capsular vessels with at least one green vessel; grade 2 is characterized by up to two capsular vessels with normal tapering, acutely angled branches, and mostly green; grade 3 is characterized by boundary zone speckle with green and red speckle being substantially equal and both red and green boundary zone speckle together being less than or equal to the amount of exterior speckle; grade 4 is characterized by boundary zone speckle with the amount of red speckle being greater than the amount of green speckle and the amount of boundary zone red speckle being greater than the amount of exterior red speckle; grade 5 is characterized by three or more red boundary zone vessels; grade 6 is characterized by boundary zone blush.

Figure 11:
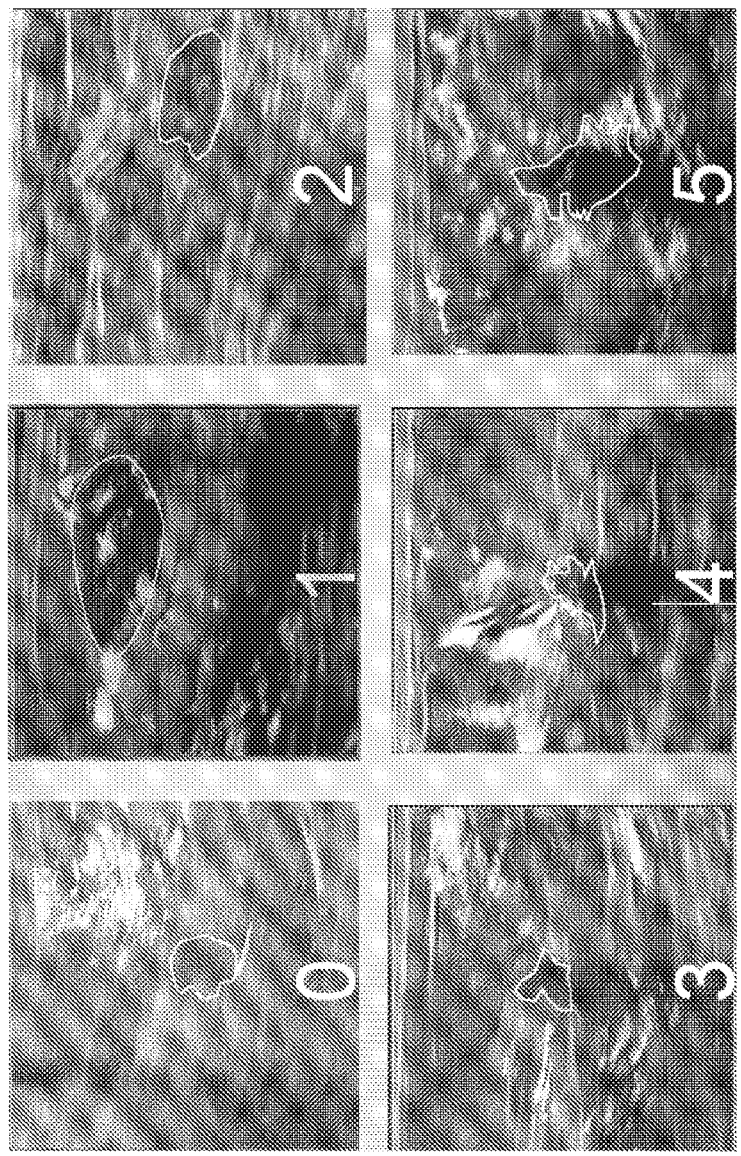
FIG. 11 shows six optoacoustic images illustrating examples of a feature presence of peripheral vessels in accordance with an embodiment of the subject invention.

FIG. 11 shows reference images for peripheral vessels grades 0-5 shown on a various optoacoustic maps. In an illustrative embodiment, grade 0 is characterized by no peritumoral vessels; grade 1 is characterized by up to two peritumoral vessels with at least one green vessel; grade 2 is characterized by more than two peritumoral vessels with random orientation (not radiating perpendicular to surface of lesion); grade 3 is characterized by one or two radiating peritumoral vessels; grade 4 is characterized by more than two radiating vessels on one side of the lesion; grade 5 is characterized by more than two radiating vessels on more than one side of the lesion.

Figure 12:
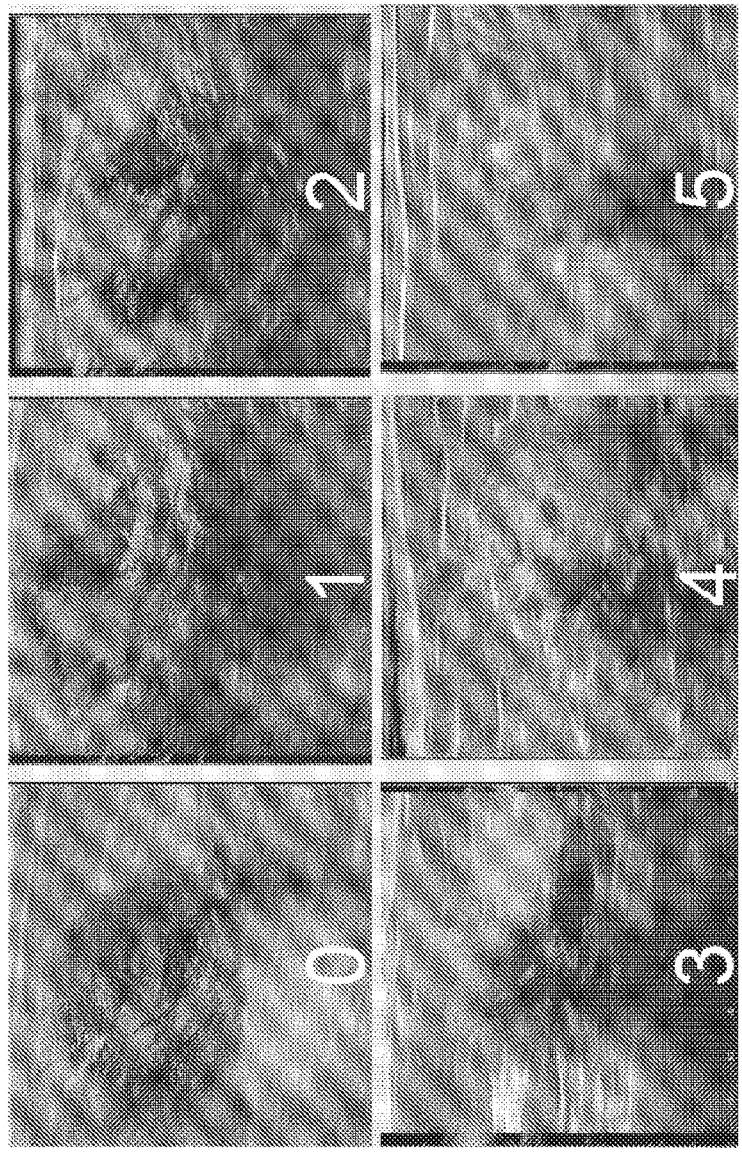
FIG. 12 shows six optoacoustic, combined map images illustrating examples of a feature interfering artifacts in accordance with an embodiment of the subject invention.

FIG. 12 shows reference images for interfering artifacts grades 0-5 shown on relative optoacoustic maps. In an illustrative embodiment, grade 0 is characterized by no significant artifacts; grade 1 is characterized by minimal artifacts, which do not interfere with grading; grade 2 is characterized by moderate artifacts, which do not interfere with grading; grade 3 is characterized by moderate artifacts, which interfere with grading; grade 4 is characterized by severe artifacts, which interfere with grading; grade 5 is characterized by severe artifacts, which make images uninterpretable.

In an embodiment, the image data or example images presented to the user are modified based on the input received from the user. In an embodiment, the image data presented to the user is modified or annotated based on the feature currently in focus. For instance, an interfering artifact identified by the system may be highlighted or radiating vessels detected on the peritumoral boundary may be annotated.

Operator Lesion Classification

In an embodiment, the operator is presented with an interface for lesion classification. In an embodiment, at 221, an operator, generally a radiologist is presented with image data, and is prompted to enter a classification. In an embodiment, the operator enters a classification of the lesion by entering text or an abbreviation for the chosen classification. In an embodiment, the operator selects a classification from a drop-down menu. Other data entry methods are known in the art and may be used. In an embodiment, the system presents one or more possible classifications of the lesion based on a plurality of feature grades entered by the operator. In an embodiment, the system presents one or more possible classifications of the lesion based on analysis previously performed by the system and/or another user. In an embodiment, the operator is able to select, confirm, or modify a lesion classification suggested by the system.

Automated Lesion Classification

In an embodiment, at a 211, the diagnostic vector classification and support system may determine a predicted value for one or more of the plurality of features that can be graded. In an embodiment, the diagnostic vector classification and support system may determine a predicted value for the six specific features identified above. A variety of different approaches may be taken. In an embodiment, image processing or other techniques are used to mimic some or all of the operator classification and grading techniques discussed above. In an embodiment, such techniques are applied in an attempt to reach the same or similar results by different means. In an embodiment, such techniques are applied toward different objectives. The techniques discussed below are illustrative examples. Other types of techniques may be used.

In an embodiment, a hemoglobin-like parametric image and an oxygenation-like parametric image are used. Such images are referred to in this section as processed images. A processed image may be filtered by one or more appropriate filters prior to feature detection. In an embodiment, one appropriate filter is a smoothing filter. In an embodiment, one appropriate filter is a shape detection filter, whereby when the shape to be detected is centered about a pixel, the filter results in a high intensity for that pixel, and when this is not the case, the intensity produced in the filtered image is low. In an embodiment, the shape detection filter is optimized to detect vessels. In an embodiment, a shape filter may be directional or include further directional information such (e.g. angle of a line or vessel). Because radiating vessels that radiate from the peritumoral region into the peripheral region may pass through the peritumoral boundary, and tend to be directed more perpendicular rather than tangent to the second boundary, a directional filter may be used to detect this condition. In an embodiment, more than one shape filter can be used.

Vascularity may be determined from a processed hemoglobin image. Oxygenation or deoxygenation may be determined from a processed oxygenation image. Thus, features involving vascularity may be found from the processed hemoglobin image. Features involving oxygenation may be found from the processed oxygenation image. Finally, a combined image parametrically reflective of deoxygenated hemoglobin masked using the image parametrically reflective of total hemoglobin (e.g., image 460) may be used, instead of, or in addition to the processed oxygenation image, to predict feature grades related to oxygenation of vessels.

To determine metrics used to quantify the presence of features for a segmented lesion, the internal, peripheral, and external region adjacent to the periphery may be used.

In an embodiment, internal deoxygenated blush is measured by determining the amount of pixels reflecting deoxygenation in the interior region. In an embodiment, the deoxygenated blush grade may be determined as a result of calculating the number of pixels that reflect deoxygenation beyond a threshold in total, or as a weighted total. In an embodiment, the deoxygenated blush grade may be determined as a result of the proportion (e.g. percentage) of the total number of pixels of the interior region that reflect deoxygenation, or deoxygenation beyond a threshold.

A parametric image or parametric image overlay may use color to illustrate a parameter. In an embodiment, the parametric image overlay (shown in image 460), can use red colors to indicate areas comprising one functional determination, i.e., concentration of deoxygenated hemoglobin, and green colors to indicate a different functional determination, i.e., areas comprising a concentration of oxygenated hemoglobin. In an embodiment, the number of red colored pixels and the number of green colored pixels may be used in lesion classification, such as grading internal deoxygenated blush. For example, in an embodiment, a weighted version of the number of internal red pixels and internal green pixels (including information about how red or how green each pixel is) may be used to produce total internal redness (weighted sum of pixels more red than a threshold), total internal greenness (weighted sum of pixels more red than a threshold), and/or a total internal metric (weighted sum of all the pixels, green positive weight and red negative weight). A ratio of internal red pixels to internal green pixels, or total redness to total greenness may be used in grading the internal deoxygenated blush.

Peritumoral boundary zone vascularity and deoxygenation may be computed by performing similar functions in the peritumoral region.

In an embodiment, other molecular indicators (beyond hemoglobin and oxygenation) may be used. In an embodiment, other molecular indicators can be determined by using different or additional predominant wavelengths to generate the stimulated response leading to the optoacoustic image.

The techniques described above may be applied to absolute contrast or (as discussed below, relative contrast) determined on the basis of the determined oxygenation and/or hemoglobin (and/or other such molecular) metric. In an embodiment, a region of interest may be used to improve contrast. Using a region of interest (as generally described in U.S. patent application Ser. No. 13/793,808, filed Mar. 11, 2013 and entitled "Statistical Mapping in an Optoacoustic Imaging System") positioned proximate to or over the lesion, may cause the colorization of the internal, periphery and external parametric image data to become more appropriate for application of the above techniques relying on colorization. Thus, the characterization techniques above may be applied on relative contrast based on statistical properties of the tissue. When relative contrast is used, the weights as described above can be determined in relation to the reference level. In an embodiment, the reference level may correspond to a weight of zero. In an embodiment, a weight of one (+1) and negative-one (−1) may correspond to values above and below the reference level. In an embodiment, the image amplitude corresponding to unity weighting magnitude (+1 or −1) may be fixed, or may be based on the statistical properties of the tissue (e.g. in proportion the standard deviation of the region of interest). In an exemplary embodiment, +1 corresponds to a pixel having its image intensity less the reference level equal to K standard deviations. In an embodiment, the reference level may be the mean of the region of interest.

Pattern classification filters may be used. In an embodiment, an image is converted to a pattern classification domain, such as a 2D wavelet packet domain. Apriori knowledge indicating when the spatial coefficients of the pattern classification domain indicate the presence of a feature in such a filter may be learned by a training phase of an algorithm. In an embodiment, such a technique uses a support vector machine (SVM), or other similar method for finding pattern clusters to produce a classifier, or other such technique. Thus, the presence of such features in an image may be quantified spatially on a per-pixel basis, and methods for counting the occurrence of such quantified measures within the defined boundaries of an image segment may be used to assess features in that zone of the image.

Artifacts, such as streaking, interferes with the determination of vessels as such artifacts may, e.g., mimic vessels. In an embodiment, a filter may be employed to suppress streaking artifact, or filter out such artifact. In an embodiment, the amount of such artifact as detected may be quantified by the filter and used as a criterion in the technique described above. In an embodiment, iterative reconstruction processing may be used to remove streaking artifacts. Many other techniques for removing artifacts from images are known in the art and can be applied by one skilled in the art.

Accordingly, in an embodiment, to compute the six features, one or more of the above-described techniques can be used:

1) internal vascularity and de-oxygenation: a score is based on the vessels detected in the hemoglobin image within the first boundary, and how oxygenated these vessels are from the oxygenation image. In an embodiment, a combined image (e.g., FIG. 4, 460) may be used. In an embodiment, a vessel detector may be used. In an embodiment, vascularity may be inferred from the amount of hemoglobin. In an embodiment, the score is related to the ratio of redness to greenness in the combined image.

2) peritumoral boundary zone vascularity and deoxygenation: a score is based on the vessels detected in the hemoglobin image within the peritumoral boundary (i.e., between the first and second boundary), and how oxygenated these vessels are from the oxygenation image. In an embodiment, a combined image (e.g., FIG. 4, 460) may be used. In an embodiment, a vessel detector may be used. In an embodiment, vascularity may be inferred from the amount of hemoglobin. In an embodiment, the score is related to the ratio of redness to greenness in the combined image.

3) internal deoxygenated blush: a score is determined as described above, for the internal region from the oxygenation image. In an embodiment, the score is related to the percentage of red pixels of the processed oxygenation map (e.g., FIG. 4, 450).

4) internal total blood: a score is determined as described above, in the internal region, from the hemoglobin image intensity, or vascular detected image. In an embodiment, the score is related to the percentage of internal pixels exceeding a threshold using the processed hemoglobin map (e.g., FIG. 4, 440).

5) external peritumoral radiating vessels: a score is determined from radiating vessels detected on the peritumoral boundary. In an embodiment, the score is related to the sum of directional filtered hemoglobin image proximate to external boundary, where such vessels near perpendicular directions to the boundary are scored high and other features are suppressed.

6) interfering artifact: a score is determined as described above. In an embodiment, artifacts are removed prior to scoring and thus, the interfering artifact score is zero.

In an embodiment, each of the foregoing features is scored on a 0-5 ordinal scale. In an embodiment, the presence of capsular/boundary zone vessels is scored on a 0-6 ordinal scale. In an embodiment, features for the ordinal scale may involve complex logic which includes conditional statements (e.g. "if") to describe ranking on the ordinal scale in certain circumstances and can use more than one such metric as described.

In an embodiment, a classification vector is formed by the scoring of each feature. The classification vector corresponds to a prediction of the classification for the lesion. In an embodiment, the classification vectors are determined empirically, by comparing computer scores for the features with histological data for a population of samples. Using this empirical method, classification vectors, which represent a summary for a population, can be updated as new classifications and histological information are available.

Diagnostic Support

In an embodiment, at 231, a classification received from a user is compared to a classification calculated by the system. In an embodiment, if the classifications differ or differ by a threshold degree, diagnostic support is provided to the user at 235. In an embodiment, if the operator and computer-generated classifications are the same or differ only by a threshold degree, the operator feature classification is output at 241. In an embodiment, diagnostic support is offered even where the operator and computer-generated classifications are already the same.

In an embodiment, at 231, a feature grade received from a user can also be compared to a feature grade calculated by the system. If the feature grades differ or differ by a threshold degree, diagnostic support may be provided to the user at 235. In an embodiment, diagnostic support is offered even where the operator and computer-generated grades are already the same. In an embodiment, if the operator and computer-generated grades are the same or differ only by a threshold degree, the operator feature grade is output at 241. In an embodiment, where the difference in operator and computer-generated feature grades would not affect the resulting classification of the tumor, diagnostic support is not offered and the method proceeds to 241.

As further discussed below, diagnostic support 235 may include presenting additional information to the user, soliciting additional input from the user, or both. In an embodiment, less information is presented to the user to focus the user on particular information.

In an embodiment, where a classification or feature grade received from the user differs or differs substantially from a classification or feature grade calculated by the system, the system presents additional image data, example images, or other information to the operator. For example, in an embodiment, the system highlights or otherwise annotates the image data displayed to emphasize information that formed the basis of the system's classification or grading. In an embodiment, the system displays a subset or portion of the image data to focus the operator on information that formed the basis of the system's classification or grading. In an embodiment, the system displays additional images to the operator. For example, in an embodiment, the system displays example images as discussed above. In an embodiment, the system displays additional image data to the operator.

In an embodiment, where a classification or feature grade received from the user differs or differs substantially from a classification or feature grade calculated by the system, the system solicits additional input from the operator. Such solicitation may occur before, after, during, or instead of the presentation of additional information to the operator. For example, in an embodiment, the operator is asked to grade or re-grade one or more features of the lesion. In an embodiment, the operator is asked to select portions of the image that formed the basis of the operator's grading of the feature. In an embodiment, the operator is asked to confirm, modify, or augment first or second boundary curves and/or segmentation of images. In an embodiment, the operator may provide such additional information regardless of whether the operator's classification or feature grades differ from those calculated by the system. In an embodiment, the system solicits such additional information regardless of whether the operator's classification or feature grades differ from those calculated by the system. In an embodiment, the operator may provide such additional information regardless of whether the system solicits it.

In an embodiment, the system may then re-evaluate one or more features of the lesion and/or its classification of the lesion based on any additional information provided by the operator, for example a modified boundary, image segmentation, or feature grade. The system may then once again display additional image data or solicit additional input from the operator.

In an embodiment, the operator may confirm the operator's classification or feature grades during diagnostic support 235. In an embodiment, reconfirmation of causes the method to terminate by returning the confirmed conclusions at 241. In an embodiment, the system requires two or more confirmations or re-confirmations before the method terminates with the confirmed values.

In an embodiment, the operator modifies the operator's classification or feature grades during diagnostic support 235 and the method returns to 231 to compare the modified classification or feature grade to the classification or feature grades computed by the system. If the modified operator classification or feature grade now match or substantially match the computed classification or feature grade, the method terminates by returning the modified operator classification or feature grade at 241.

In an embodiment, the operator confirms one or more of the computed classifications or feature grades, which causes a positive comparison at 231, and termination with return of the confirmed classification or feature grade at 241.

Study

A further illustrative embodiment is described below with reference to a study using opto-acoustics (OA), a dual energy laser technology co-registered with diagnostic ultrasound to simultaneously assess structural and functional features of breast masses. OA requires no injected agent and utilizes no radiation. A description of an optoacoustic device and its features can be found in the Parametric Map Application.

A study was conducted concerning a new method and system for how to use OA features to classify breast masses as malignant or benign. In an embodiment, six specific OA features were assessed using a 0-5 ordinal scale:

1) internal vascularity and de-oxygenation,
2) peri-tumoral boundary zone vascularity and deoxygenation,
3) internal deoxygenated blush,
4) internal total blood,
5) external peri-tumoral radiating vessels, and
6) interfering artifact.

Analyses were performed using: Logistic Regression (LR), Support Vector Machines (SVM), Classification Trees (CT), Random Forests (RF), and K-Nearest Neighbors (KNN). Ten-fold cross validation was used, where the 66 cases were randomly divided into 10 groups. Each group was removed in turn from the 66 observations and the classifier was trained on the remaining groups to develop a classification rule. This rule was then applied to the removed group. This was repeated 10 times until every observation was assigned by a classifier that had not previously been developed using that observation.

Results

Sensitivity and specificity assessments by each method are summarized in the table below. KNN and SVM performed the best, while LR performed the worst, but the results were consistent and favorable for all 5 analyses; sensitivity ranged from 95% to 100% and specificity ranged from 52% to 79%. Findings support the biopsy-sparing potential for OA imaging.

| Method | Malignant Classified as Benign | Benign Classified as Cancer | Sensitivity | Specificity |
|---|---|---|---|---|
| Logistic Regression | 2 | 14 | 95% | 52% |
| Support Vector Machine | 0 | 6 | 100% | 79% |
| Classification Trees | 1 | 10 | 97% | 66% |
| Random Forest | 0 | 8 | 100% | 72% |
| K Nearest Neighbor | 0 | 6 | 100% | 79% |

Data suggest that new method of analysis of breast masses using OA image can achieve clinically meaningful sensitivity and specificity in a diagnostic setting.

Summary

Analysis yields sets of features that can cluster the data (only IDC and FA were examined) in to three clusters: cluster #1 is FA, cluster #2 is IDC-GR1, cluster #3 is IDC-GR2, IDC-GR3 (and a small number of ILC-GR2). In general, this is consistent with the rules as proposed by Dr. Stavros. This report may further formalize that analysis, or provide more insight into the use of the rule sets.

Method

Figure 13B:
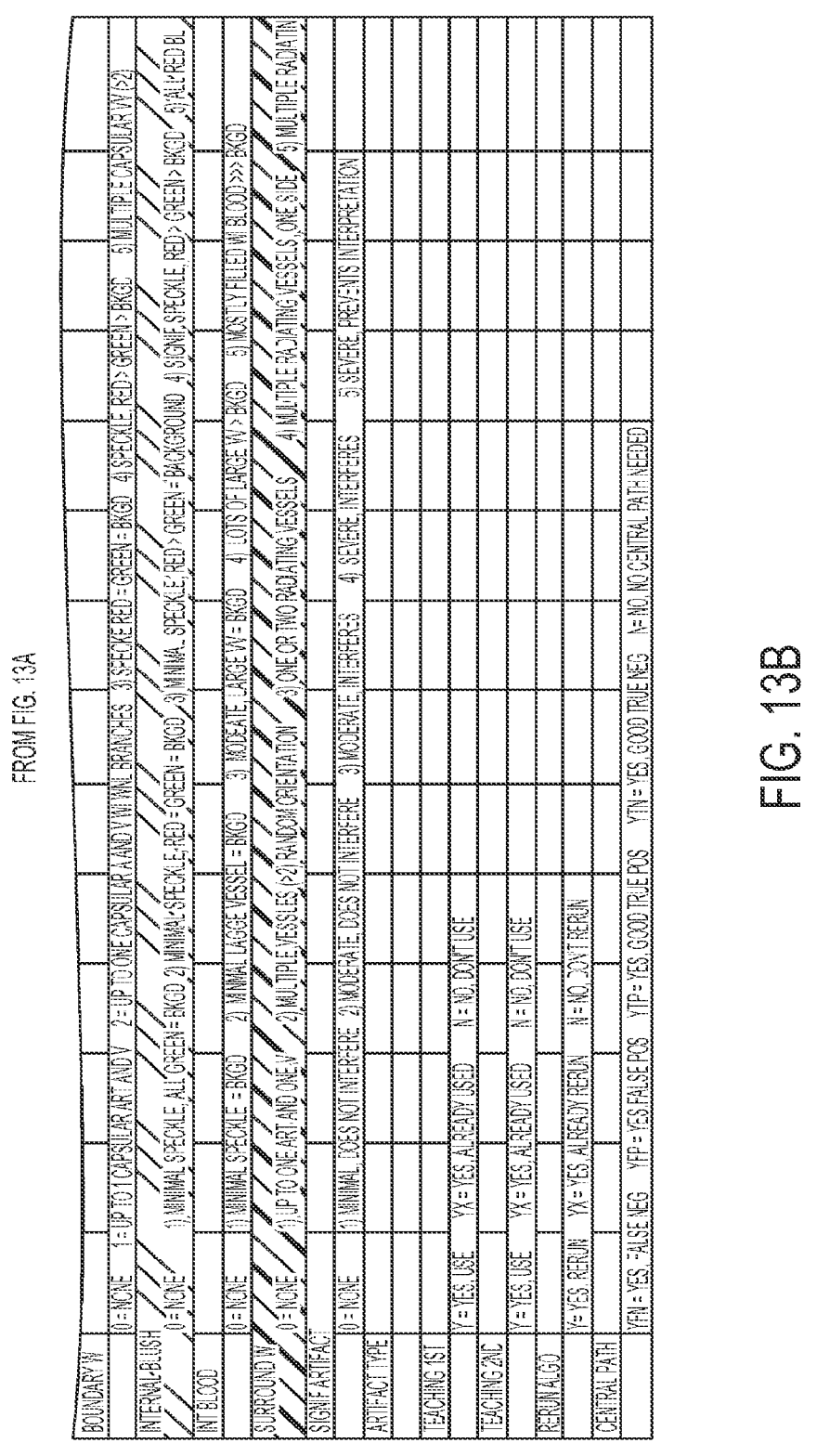

Features were selected and ranked (from values 1 to 5). The ranking criterion used was shown in FIGS. 13A and 13B. An analysis was done on FA and IDC-GR1, IDC-GR2 and IDC-GR3 patients to determine what criteria are significant to distinguish the two classes. The matlab anova analysis tool was used. The results is presented in an informal format.

Data

The data contained graded contained a subset 80 patients. Of these 80 patients, there were 13 that were not graded yet (incomplete). Of the 80, there were 28 FA, 3 ILC and 48 IDC. There were 51 malignants and 29 benigns. For the malignants, there were 11 GR1, 18 GR2, and 22GR3. Data from the other types of lesions encountered in the feasibility study were not yet graded on the spreadsheet for input to this analysis, and hence was not analyzed.

Observations

Figure 14A:
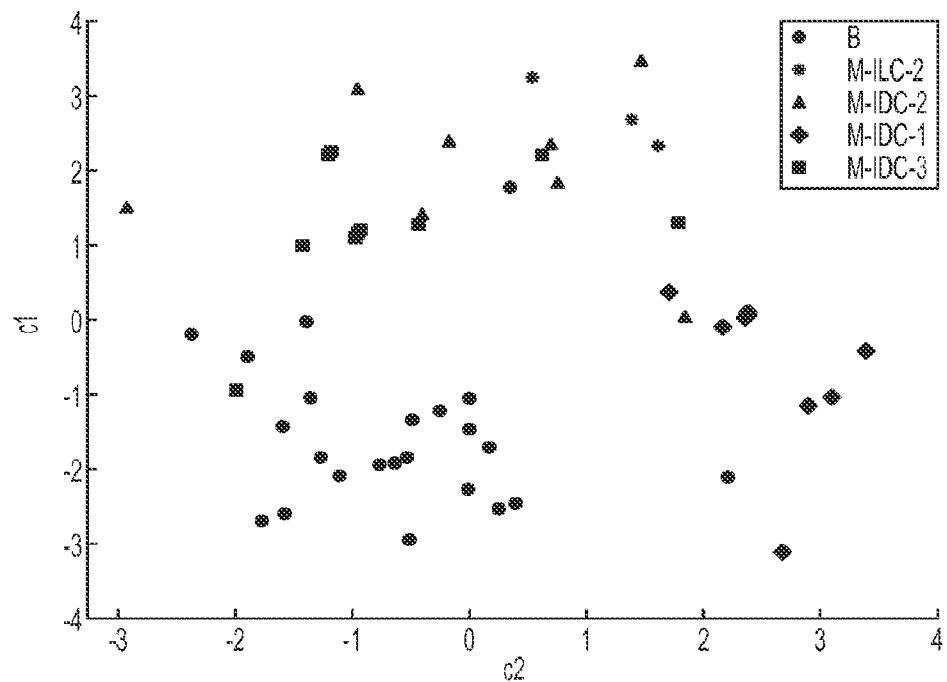
FIGS. 14A and 14B shows a scatter plot of various features in accordance with an embodiment of the subject invention.
Figure 14B:
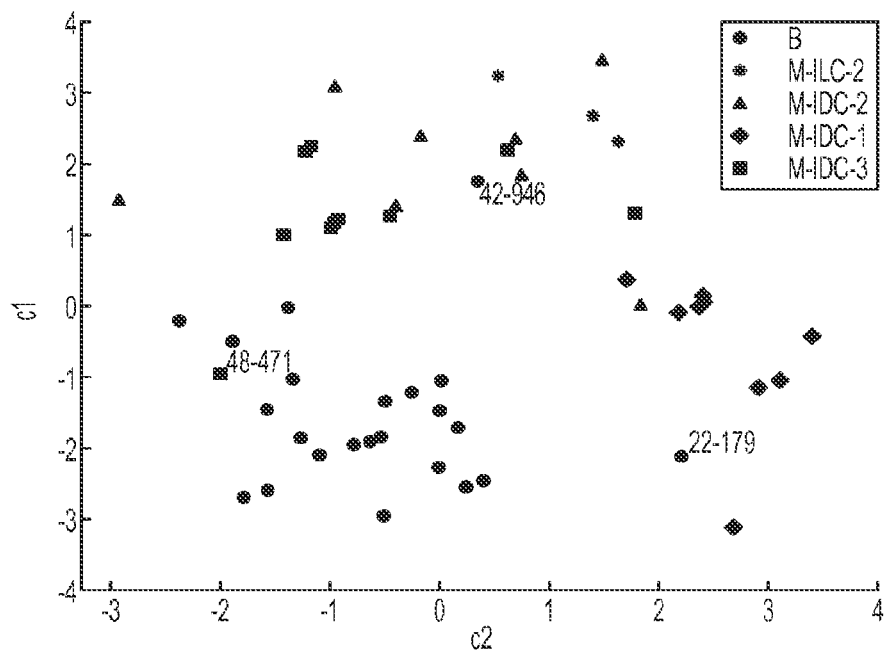
Figure 15:
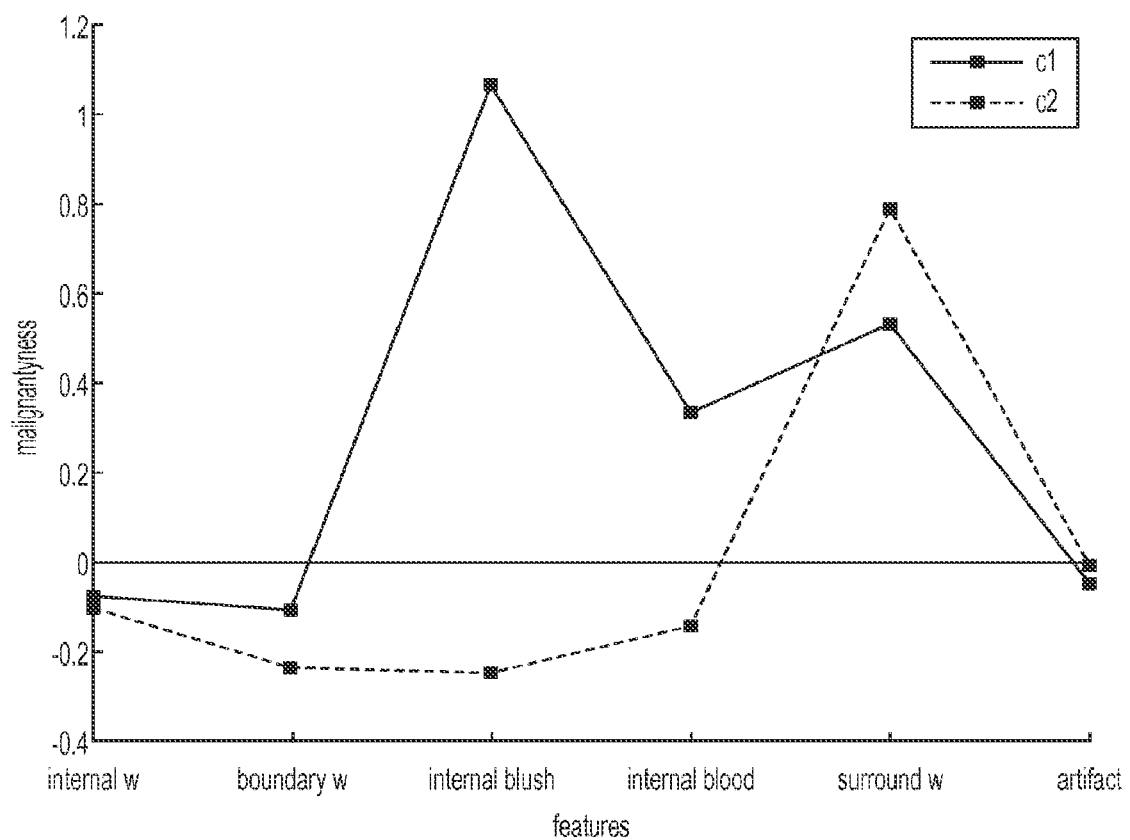
FIG. 15 shows feature vectors with the strongest correlation between features in accordance with an embodiment of the subject invention.

FIGS. 14A and 14B show a scatter plot of the features. Each red dot represents a patient. The red dots are benign patients. The benign patients cluster into the bottom left of the image. The x-axis represents a score based on feature vector c2. The y-axis represents a score based on feature vector c1. Each feature vector represents a combination of features where the weights were solved by the ANOVA analysis. Feature vectors c1 and c2 are shown in FIG. 15. In FIG. 2b, the patient IDs of the outliers is shown.

From FIG. 15, feature vector c2 detects if patient contains mainly the following: low internal vv, low boundary vv, low internal blush, low internal blood, and permitting a small amount of surround vv. If the combination of these features are mainly present, then the c2 score will indicate that the diagnosis is likely not an IDC-GR3 when choosing between a FA and an IDC. Feature vector c2 was the second best predictor determined from the ANOVA analysis. However, feature vector c2 in is also able to cluster the IDC-GR1s apart from the benigns on the x-axis.

Also from FIG. 15, feature vector c1 (the highest predictor) detects if a patient contains mainly the following: any internal blush (internal blush is most highly weighted in the graph), significant surround vv, and a large amount of internal blood. With a low score on feature vector c1, IDC-GR1 and IDC-GR2 and ILC-GR2 can be separated from the category of both FA and IDC-GR1 (y-axis).

CONCLUSIONS

The analysis yields sets of features that can cluster the data (when choosing between IDC and FA) in to three clusters: cluster #1 is FA, cluster #2 is IDC-GR1, cluster #3 is IDC-GR2, IDC-GR3 and ILC-GR2. In general, this is consistent with the rules as proposed by Dr. Stavros. Complimentary information may be yielded in this analysis.

The features listed in c1 and c2 may be used to assist in the diagnosis of OA information.

Patients primarily where patient contains mainly the following (c2 vector): low internal vv, low boundary vv, low internal blush, low internal blood, and permitting a small amount of surround vv can be grouped into a class that will distinguish IDC-GR1 from other classes. Patients images that contain mainly the following: any internal blush (internal blush is most highly weighted in the graph), significant surround vv, and a large amount of internal blood can be grouped into a class that will distinguish IDC-GR1 from other classes.

NOTE

Ultrasound features were not considered in this analysis. In many cases ultrasound features may be necessary to distinguish different lesions, and determine under what situations optoacoustic features are applicable.

Those skilled in the art will recognize that the methods and systems of the present disclosure may be implemented in many manners and as such are not to be limited by the foregoing exemplary embodiments and examples. In other words, functional elements being performed by single or multiple components (or sub-systems), in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, sub-systems, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

The invention claimed is:

1. A method for evaluating a tumor having a central nidus and a peritumoral region adjacent to the central nidus, the method comprising:
presenting on a display an optoacoustic image of at least a portion of a volume of tissue comprising the tumor, wherein the optoacoustic image comprises image information representative of a response, by at least the portion of the volume of tissue, to one or more wavelengths of light;
identifying on the display a boundary zone of the tumor within the optoacoustic image, the boundary zone approximating at least a portion of the peritumoral region of the tumor; and
obtaining a feature grade, from at least one of i) an operator or ii) automatically from a computer model, for at least one peritumoral feature contained at least partially within the boundary zone of the tumor within the optoacoustic image.

2. The method of claim 1, further comprising obtaining at least one additional feature grade for the at least one peritumoral feature contained at least partially within the boundary zone, wherein the at least one additional feature grade is obtained by calculating by computer one or more computer-generated feature grades for the at least one peritumoral feature, the one or more computer-generated feature grades being based, at least in part, on information falling within the boundary zone.

3. The method of claim 1, further comprising:
obtaining, from an operator, a revised boundary zone, and
re-calculating by the computer the feature grade for the at least one peritumoral feature, the feature grade being based, at least in part, on information falling within a revised boundary zone.

4. The method of claim 1, further comprising:
obtaining one or more supplementary inputs from the operator, wherein at least one of the one or more supplementary inputs is a revised boundary zone, the method further comprising:
re-calculating by the computer the feature grade for the at least one peritumoral feature, the feature grade being based, at least in part, on information falling within the revised boundary zone; and
re-obtaining the one or more supplementary inputs from the operator when an operator feature grade differs from a computer-generated feature grade.

5. The method of claim 4, wherein at least one of the one or more supplementary inputs is a modification to the operator feature grade, the method further comprising re-obtaining the one or more supplementary inputs from the operator when the operator feature grade differs from the computer-generated feature grade.

6. The method of claim 4, wherein the at least one of the one or more supplementary inputs is a confirmation of the feature grade.

7. The method of claim 4, wherein the at least one of the one or more supplementary inputs is the operator feature zone, the method further comprising:
calculating by the computer the computer-generated feature grade for the at least one peritumoral feature, based at least in part on information falling within the feature zone; and
re-obtaining the one or more supplementary inputs from the operator when the operator feature grade differs from the computer-generated feature grade.

8. The method of claim 1, further comprising obtaining at least one additional feature grade from another operator.

9. The method of claim 1, wherein the optoacoustic image comprises image information representative of a response, by at least the portion of the volume of tissue, to short and long predominant wavelengths of light.

10. The method of claim 1, wherein the optoacoustic image comprises image information representative of a response, by at least the portion of the volume of tissue, to a first predominant wavelength of light.

11. The method of claim 10, wherein the optoacoustic image comprises image information representative of a response, by at least the portion of the volume of tissue, to a first predominant wavelength of light.

12. The method of claim 1, wherein the optoacoustic image includes information indicative of at least one of: 1) internal de-oxygenation, 2) peritumoral boundary zone deoxygenation, 3) internal deoxygenated blush, or 4) internal total blood, and wherein the feature grade, at least in part, scores the at least one of: 1) internal de-oxygenation, 2) peritumoral boundary zone deoxygenation, 3) internal deoxygenated blush, or 4) internal total blood.

13. A method for evaluating a tumor having a central nidus and a peritumoral region adjacent to the central nidus, the method comprising:
   presenting on a display an optoacoustic image of at least a portion of a volume of tissue comprising the tumor, wherein the optoacoustic image includes deoxygenation information indicative of de-oxygenation for at least the portion of the volume of tissue, the deoxygenation information determined at least in part from a response, by at least the portion of the volume of tissue, to one or more wavelengths of light;
   identifying on the display a boundary zone of the tumor within the optoacoustic image, the boundary zone approximating at least a portion of the peritumoral region of the tumor; and
   obtaining a feature grade, from at least one of i) an operator or ii) automatically from a computer model, for at least one peritumoral feature contained at least partially within the boundary zone of the tumor within the optoacoustic image.

14. The method of claim 13, wherein the feature grade includes an operator feature grade from the operator and a computer-generated features grade score obtained automatically, the method further comprising:
   comparing the operator feature grade and the computer-generated feature grade; and
   obtaining one or more supplementary inputs from the operator when the operator feature grade differs from the computer-generated feature grade.

15. The method of claim 13, further comprising:
   obtaining, from an operator, a revised boundary zone, and
   calculating by the computer the feature grade based, at least in part, on information falling within the revised boundary zone.

16. The method of claim 13, wherein the optoacoustic image comprises image information representative of a response, by at least the portion of the volume of tissue, to short and long predominant wavelengths of light.

17. The method of claim 13, wherein the optoacoustic image comprises image information representative of a response, by at least the portion of the volume of tissue, to a first predominant wavelength of light.

18. The method of claim 13, wherein the optoacoustic image comprises image information representative of a response, by at least the portion of the volume of tissue, to a first predominant wavelength of light.

* * * * *